(12) United States Patent
Arkenau-Maric et al.

(10) Patent No.: US 8,192,722 B2
(45) Date of Patent: *Jun. 5, 2012

(54) ABUSE-PROOF DOSAGE FORM

(75) Inventors: Elisabeth Arkenau-Maric, Köln (DE);
Johannes Bartholomaus, Aachen (DE);
Heinrich Kugelmann, Aachen (DE)

(73) Assignee: Grunenthal GmbH, Aachen (DE)

( * ) Notice: Subject to any disclaimer, the term of this patent is extended or adjusted under 35 U.S.C. 154(b) by 664 days.

This patent is subject to a terminal disclaimer.

(21) Appl. No.: 12/140,665

(22) Filed: Jun. 17, 2008

(65) Prior Publication Data

US 2008/0311049 A1    Dec. 18, 2008

Related U.S. Application Data

(60) Division of application No. 11/462,216, filed on Aug. 3, 2006, which is a continuation-in-part of application No. 11/349,544, filed on Feb. 6, 2006, which is a continuation-in-part of application No. 11/348,295, filed on Feb. 6, 2006, which is a continuation-in-part of application No. 10/718,112, filed on Nov. 20, 2003.

(30) Foreign Application Priority Data

Aug. 6, 2003   (DE) ................................ 10 336 400
Feb. 4, 2005   (DE) .......................... 10 2005 005 446

(51) Int. Cl.
*A61K 31/485* (2006.01)
*A61K 9/20* (2006.01)
*A61K 49/00* (2006.01)
*A61K 9/14* (2006.01)
*A01N 43/42* (2006.01)

(52) U.S. Cl. ........ 424/10.1; 424/465; 424/484; 514/282

(58) Field of Classification Search ................. 424/10.1, 424/465, 484; 514/282
See application file for complete search history.

(56) References Cited

U.S. PATENT DOCUMENTS

| | | |
|---|---|---|
| 3,806,603 A | 4/1974 | Gaunt et al. |
| 3,865,108 A | 2/1975 | Hartop |
| 3,966,747 A | 6/1976 | Monkovic et al. |
| 3,980,766 A | 9/1976 | Shaw et al. |
| 4,002,173 A | 1/1977 | Manning et al. |
| 4,014,965 A | 3/1977 | Stube et al. |
| 4,070,494 A | 1/1978 | Hoffmeister et al. |

(Continued)

FOREIGN PATENT DOCUMENTS

AR          46994        12/2004

(Continued)

OTHER PUBLICATIONS

V.K. Thoma et al., "Bestimmung der In-vitro-Freigabe von schwach basischen Wirkstoffen aus Retardarzneiformen," Pharm. Ind. 51, Nr. 3 (1989).

(Continued)

*Primary Examiner* — Robert A Wax
*Assistant Examiner* — Aradhana Sasan
(74) *Attorney, Agent, or Firm* — Norris McLaughlin & Marcus, P.A.

(57) ABSTRACT

The invention relates to a dosage form that is thermoformed without discoloration and is safeguarded from abuse, comprising at least one synthetic or natural polymer having a breaking strength of at least 500 N in addition to one or more active substances that could be subject to abuse. The invention also relates to a corresponding method for producing said dosage form.

27 Claims, 2 Drawing Sheets

U.S. PATENT DOCUMENTS

| | | |
|---|---|---|
| 4,070,497 A | 1/1978 | Wismer et al. |
| 4,175,119 A | 11/1979 | Porter |
| 4,200,704 A | 4/1980 | Stanley et al. |
| 4,207,893 A | 6/1980 | Michaels |
| 4,262,017 A | 4/1981 | Kuipers et al. |
| 4,343,789 A | 8/1982 | Kawata et al. |
| 4,353,887 A | 10/1982 | Hess |
| 4,404,183 A | 9/1983 | Kawata et al. |
| 4,427,681 A | 1/1984 | Munshi |
| 4,462,941 A | 7/1984 | Lee et al. |
| 4,603,143 A | 7/1986 | Schmidt |
| 4,612,008 A | 9/1986 | Wong et al. |
| 4,629,621 A | 12/1986 | Snipes |
| 4,690,822 A | 9/1987 | Uemura et al. |
| 4,713,243 A | 12/1987 | Schiraldi et al. |
| 4,744,976 A | 5/1988 | Snipes et al. |
| 4,764,378 A | 8/1988 | Keith et al. |
| 4,765,989 A | 8/1988 | Wong et al. |
| 4,774,074 A | 9/1988 | Snipes |
| 4,783,337 A | 11/1988 | Wong et al. |
| 4,806,337 A | 2/1989 | Snipes et al. |
| RE33,093 E | 10/1989 | Schiraldi et al. |
| 4,880,585 A | 11/1989 | Klimesch et al. |
| 4,892,778 A | 1/1990 | Theeuwes et al. |
| 4,892,889 A | 1/1990 | Kirk et al. |
| 4,940,556 A | 7/1990 | MacFarlane et al. |
| 4,957,668 A | 9/1990 | Plackard et al. |
| 4,957,681 A | 9/1990 | Klimesch et al. |
| 4,960,814 A | 10/1990 | Wu et al. |
| 4,992,278 A | 2/1991 | Khanna |
| 4,992,279 A | 2/1991 | Palmer et al. |
| 5,004,601 A | 4/1991 | Snipes |
| 5,051,261 A | 9/1991 | McGinity et al. |
| 5,169,645 A | 12/1992 | Shukla et al. |
| 5,198,226 A | 3/1993 | MacFarlane et al. |
| 5,200,197 A | 4/1993 | Wright et al. |
| 5,211,892 A | 5/1993 | Gueret et al. |
| 5,273,758 A | 12/1993 | Royce |
| 5,350,741 A | 9/1994 | Takada |
| 5,378,462 A | 1/1995 | Boedecker et al. |
| 5,427,798 A | 6/1995 | Ludwig et al. |
| RE34,990 E | 7/1995 | Khanna et al. |
| 5,458,887 A | 10/1995 | Chen et al. |
| 5,460,826 A | 10/1995 | Merrill et al. |
| 5,556,640 A | 9/1996 | Ito et al. |
| 5,562,920 A | 10/1996 | Demmer et al. |
| 5,601,842 A | 2/1997 | Bartholomaeus |
| 5,620,697 A | 4/1997 | Tormala et al. |
| 5,681,517 A | 10/1997 | Metzger |
| 5,741,519 A | 4/1998 | Rosenberg et al. |
| 5,792,474 A | 8/1998 | Rauchfuss |
| 5,801,201 A | 9/1998 | Graudums et al. |
| 5,811,126 A | 9/1998 | Krishnamurthy |
| 5,849,240 A | 12/1998 | Miller et al. |
| 5,866,164 A | 2/1999 | Kuczynski et al. |
| 5,916,584 A | 6/1999 | O'Donoghue et al. |
| 5,928,739 A | 7/1999 | Pophusen et al. |
| 5,939,099 A | 8/1999 | Grabowski et al. |
| 5,945,125 A | 8/1999 | Kim |
| 5,948,787 A | 9/1999 | Merrill et al. |
| 5,968,925 A | 10/1999 | Knidlberger |
| 6,001,391 A | 12/1999 | Zeidler et al. |
| 6,009,390 A | 12/1999 | Gupta et al. |
| 6,009,690 A | 1/2000 | Rosenberg et al. |
| 6,077,538 A | 6/2000 | Merrill et al. |
| 6,096,339 A | 8/2000 | Ayer et al. |
| 6,117,453 A | 9/2000 | Seth et al. |
| 6,120,802 A | 9/2000 | Breitenbach et al. |
| 6,133,241 A | 10/2000 | Bok et al. |
| 6,228,863 B1 | 5/2001 | Palermo et al. |
| 6,235,825 B1 | 5/2001 | Yoshida et al. |
| 6,238,697 B1 | 5/2001 | Kumar et al. |
| 6,245,357 B1 | 6/2001 | Edgren et al. |
| 6,248,737 B1 | 6/2001 | Buschmann et al. |
| 6,261,599 B1 | 7/2001 | Oshlack et al. |
| 6,290,990 B1 | 9/2001 | Grabowski et al. |
| 6,306,438 B1 | 10/2001 | Oshlack et al. |
| 6,309,668 B1 | 10/2001 | Bastin et al. |
| 6,318,650 B1 | 11/2001 | Breitenbach et al. |
| 6,340,475 B2 | 1/2002 | Shell et al. |
| 6,344,535 B1 | 2/2002 | Timmermann et al. |
| 6,348,469 B1 | 2/2002 | Seth |
| 6,375,963 B1 | 4/2002 | Repka et al. |
| 6,399,100 B1 | 6/2002 | Clancy et al. |
| 6,419,954 B1 | 7/2002 | Chu et al. |
| 6,436,441 B1 | 8/2002 | Sako et al. |
| 6,461,644 B1 | 10/2002 | Jackson et al. |
| 6,488,962 B1 | 12/2002 | Berner et al. |
| 6,488,963 B1 | 12/2002 | McGinity et al. |
| 6,534,089 B1 | 3/2003 | Ayer et al. |
| 6,547,997 B1 | 4/2003 | Breitenbach et al. |
| 6,562,375 B1 | 5/2003 | Sako et al. |
| 6,592,901 B2 | 7/2003 | Durig et al. |
| 6,635,280 B2 | 10/2003 | Shell et al. |
| 6,699,503 B1 | 3/2004 | Sako et al. |
| 6,723,340 B2 | 4/2004 | Gusler et al. |
| 6,733,783 B2 | 5/2004 | Oshlack et al. |
| 6,753,009 B2 | 6/2004 | Luber et al. |
| 6,821,588 B1 | 11/2004 | Hammer et al. |
| 7,141,250 B2 | 11/2006 | Oshlack et al. |
| 7,176,251 B1 | 2/2007 | Bastioli et al. |
| 7,776,314 B2 | 8/2010 | Bartholomäus et al. |
| 2001/0038852 A1 | 11/2001 | Kolter et al. |
| 2002/0001270 A1 | 1/2002 | Fukuchi et al. |
| 2002/0015730 A1 | 2/2002 | Hoffmann et al. |
| 2002/0051820 A1 | 5/2002 | Shell et al. |
| 2002/0114838 A1 | 8/2002 | Ayer et al. |
| 2002/0132359 A1 | 9/2002 | Waterman |
| 2002/0187192 A1 | 12/2002 | Joshi et al. |
| 2003/0008409 A1 | 1/2003 | Spearman et al. |
| 2003/0015814 A1 | 1/2003 | Krull et al. |
| 2003/0017532 A1 | 1/2003 | Biswas et al. |
| 2003/0021546 A1 | 1/2003 | Sato |
| 2003/0031546 A1 | 2/2003 | Araki et al. |
| 2003/0044458 A1 | 3/2003 | Wright, IV et al. |
| 2003/0044464 A1 | 3/2003 | Ziegler et al. |
| 2003/0064099 A1 | 4/2003 | Oshlack et al. |
| 2003/0068276 A1 | 4/2003 | Hughes et al. |
| 2003/0068370 A1 | 4/2003 | Sackler |
| 2003/0068371 A1 | 4/2003 | Oshlack et al. |
| 2003/0068392 A1 | 4/2003 | Sackler |
| 2003/0091630 A1 | 5/2003 | Louie-Helm et al. |
| 2003/0104052 A1 | 6/2003 | Berner et al. |
| 2003/0118641 A1 | 6/2003 | Maloney et al. |
| 2003/0124185 A1 | 7/2003 | Oshlack et al. |
| 2003/0125347 A1 | 7/2003 | Anderson et al. |
| 2003/0133985 A1 | 7/2003 | Louie-Helm et al. |
| 2003/0152622 A1 | 8/2003 | Louie-Helm et al. |
| 2003/0158242 A1 | 8/2003 | Kugelmann |
| 2003/0175326 A1 | 9/2003 | Thombre |
| 2003/0232895 A1 | 12/2003 | Omidian et al. |
| 2004/0010000 A1 | 1/2004 | Ayer et al. |
| 2004/0011806 A1 | 1/2004 | Luciano et al. |
| 2004/0052731 A1 | 3/2004 | Hirsh et al. |
| 2004/0052844 A1 | 3/2004 | Hsiao et al. |
| 2004/0081694 A1 | 4/2004 | Oshlack et al. |
| 2004/0091528 A1 | 5/2004 | Rogers et al. |
| 2004/0131671 A1 | 7/2004 | Zhang et al. |
| 2004/0156899 A1 | 8/2004 | Louie-Helm et al. |
| 2004/0170567 A1 | 9/2004 | Sackler |
| 2004/0185105 A1 | 9/2004 | Berner et al. |
| 2004/0213848 A1 | 10/2004 | Li et al. |
| 2005/0015730 A1 | 1/2005 | Gunturi et al. |
| 2005/0031546 A1 | 2/2005 | Bartholomaus et al. |
| 2005/0058706 A1 | 3/2005 | Bartholomaeus et al. |
| 2005/0063214 A1 | 3/2005 | Takashima |
| 2005/0089475 A1 | 4/2005 | Gruber |
| 2005/0095291 A1 | 5/2005 | Oshlack et al. |
| 2005/0106249 A1 | 5/2005 | Hwang et al. |
| 2005/0112067 A1 | 5/2005 | Kumar et al. |
| 2005/0127555 A1 | 6/2005 | Gusik et al. |
| 2005/0152843 A1 | 7/2005 | Bartholomaeus et al. |
| 2005/0186139 A1 | 8/2005 | Bartholomaeus et al. |
| 2005/0191244 A1 | 9/2005 | Bartholomaus et al. |
| 2005/0214223 A1 | 9/2005 | Bartholomaus et al. |
| 2005/0236741 A1 | 10/2005 | Arkenau-Maric et al. |
| 2005/0266084 A1 | 12/2005 | Li et al. |

| | | | | | |
|---|---|---|---|---|---|
| 2006/0002859 A1 | 1/2006 | Arkenau et al. | CN | 101010071 | 6/2005 |
| 2006/0002860 A1 | 1/2006 | Bartholomaus et al. | CN | 101022787 | 1/2006 |
| 2006/0039864 A1 | 2/2006 | Bartholomaus et al. | CN | 001863513 | 11/2006 |
| 2006/0099250 A1 | 5/2006 | Tian et al. | CN | 001863514 | 11/2006 |
| 2006/0188447 A1 | 8/2006 | Arkenau-Maric et al. | CN | 01917862 | 2/2007 |
| 2006/0193782 A1 | 8/2006 | Bartholomaus et al. | CN | 101027044 | 8/2007 |
| 2006/0193914 A1 | 8/2006 | Ashworth et al. | CN | 101111232 | 1/2008 |
| 2006/0240110 A1 | 10/2006 | Kiick et al. | CN | 101175482 | 2/2008 |
| 2007/0003616 A1 | 1/2007 | Arkenau-Maric et al. | DE | 2530563 | 1/1977 |
| 2007/0020188 A1 | 1/2007 | Sackler | DE | 4309528 | 9/1994 |
| 2007/0020335 A1 | 1/2007 | Chen et al. | DE | 69400215 | 10/1996 |
| 2007/0048228 A1 | 3/2007 | Arkenau-Maric et al. | DE | 195 22 899 | 12/1996 |
| 2007/0065365 A1 | 3/2007 | Kugelmann et al. | DE | 2808505 | 1/1997 |
| 2007/0092573 A1 | 4/2007 | Joshi et al. | DE | 19822979 | 2/1999 |
| 2007/0183979 A1 | 8/2007 | Arken Au-Maric et al. | DE | 19753534 | 6/1999 |
| 2007/0183980 A1 | 8/2007 | Arkenau-Maric et al. | DE | 19800689 C1 | 7/1999 |
| 2007/0190142 A1 | 8/2007 | Breitenbach et al. | DE | 19800698 | 7/1999 |
| 2007/0196396 A1 | 8/2007 | Pilgaonkar et al. | DE | 69229881 | 12/1999 |
| 2007/0196481 A1 | 8/2007 | Amidon et al. | DE | 19856147 | 6/2000 |
| 2007/0264327 A1 | 11/2007 | Kumar et al. | DE | 19940740 | 3/2001 |
| 2007/0269505 A1 | 11/2007 | Flath et al. | DE | 1996 0494 A1 | 6/2001 |
| 2008/0081290 A1 | 4/2008 | Wada et al. | DE | 10036400 | 6/2002 |
| 2008/0247959 A1 | 10/2008 | Bartholomaus et al. | DE | 19855440 | 6/2002 |
| 2008/0248113 A1 | 10/2008 | Bartholomaus et al. | DE | 69429710 | 8/2002 |
| 2008/0311049 A1 | 12/2008 | Arkenau-Maric et al. | DE | 10250083 | 12/2003 |
| 2008/0311187 A1 | 12/2008 | Ashworth et al. | DE | 10 250 087 A1 | 5/2004 |
| 2008/0311197 A1 | 12/2008 | Arkenau-Maric et al. | DE | 10250084 | 5/2004 |
| 2008/0312264 A1 | 12/2008 | Arkenau-Maric et al. | DE | 10250088 | 5/2004 |
| 2008/0317854 A1 | 12/2008 | Arkenau et al. | DE | 10336400 | 3/2005 |
| 2009/0004267 A1 | 1/2009 | Arkenau-Maric et al. | DE | 102004019916 | 11/2005 |
| 2009/0005408 A1 | 1/2009 | Arkenau-Maric et al. | DE | 102004020220 | 11/2005 |
| 2009/0017121 A1 | 1/2009 | Berner et al. | DE | 10 2004 032049 A1 | 1/2006 |
| 2009/0081290 A1 | 3/2009 | McKenna et al. | DE | 10 2004 032051 | 1/2006 |
| 2009/0202634 A1 | 8/2009 | Jans et al. | DE | 10 2004 032103 A1 | 1/2006 |
| 2010/0015223 A1 | 1/2010 | Cailly-Dufestel et al. | DE | 10 2005 005446 | 8/2006 |
| 2010/0098758 A1 | 4/2010 | Bartholomaus et al. | DE | 10 2005 005449 A1 | 8/2006 |
| 2010/0151028 A1 | 6/2010 | Ashworth et al. | DE | 102007011485 | 9/2008 |
| 2010/0221322 A1 | 9/2010 | Bartholomaus et al. | DK | 1658055 | 7/2007 |
| 2010/0260833 A1 | 10/2010 | Bartholomaus et al. | DK | 1658054 | 10/2007 |
| 2011/0020451 A1 | 1/2011 | Bartholomaus et al. | DK | 1515702 | 1/2009 |
| 2011/0038930 A1 | 2/2011 | Barnscheid et al. | EC | SP066345 | 8/2006 |
| 2011/0082214 A1 | 4/2011 | Faure et al. | EP | 0 008 131 | 2/1980 |
| | | | EP | 0 043 254 | 1/1982 |
| FOREIGN PATENT DOCUMENTS | | | EP | 0177893 | 4/1986 |
| AR | 045353 | 10/2005 | EP | 0 216 453 | 4/1987 |
| AR | 049562 | 8/2006 | EP | 0 226 061 | 6/1987 |
| AR | 053304 | 5/2007 | EP | 0 228 417 | 7/1987 |
| AR | 054222 | 6/2007 | EP | 0 229 652 | 7/1987 |
| AR | 054328 | 6/2007 | EP | 0 232 877 | 8/1987 |
| AU | 2003237944 | 12/2003 | EP | 0240906 A2 | 10/1987 |
| AU | 2003274071 | 5/2004 | EP | 0 261 616 | 3/1988 |
| AU | 2003278133 | 5/2004 | EP | 2 70 954 A1 | 6/1988 |
| AU | 2003279317 | 5/2004 | EP | 0 277 289 | 8/1988 |
| AU | 2004264667 | 2/2005 | EP | 0 293 066 | 11/1988 |
| AU | 2004308653 | 4/2005 | EP | 0 328 775 | 8/1989 |
| AU | 2005259476 | 1/2006 | EP | 0 477 135 | 3/1992 |
| AU | 2005259478 | 1/2006 | EP | 0544144 A1 | 6/1993 |
| AU | 2006210145 | 8/2006 | EP | 0 583 726 | 2/1994 |
| AU | 2009207796 | 7/2009 | EP | 0 598 606 | 5/1994 |
| AU | 2004264666 B2 | 10/2009 | EP | 0636370 A1 | 2/1995 |
| AU | 2009243681 | 11/2009 | EP | 0 641 195 | 3/1995 |
| BR | PI0413318 | 10/2006 | EP | 0647448 A1 | 4/1995 |
| BR | PI0413361 | 10/2006 | EP | 0682945 | 5/1995 |
| BR | PI0513300 | 5/2008 | EP | 0 661 045 | 7/1995 |
| BR | PI0606145 | 2/2009 | EP | 0661045 | 7/1995 |
| CA | 2317747 | 7/1999 | EP | 0675710 A1 | 10/1995 |
| CA | 2352874 A1 | 6/2000 | EP | 0693475 | 1/1996 |
| CA | 2502965 A1 | 5/2004 | EP | 0820693 | 1/1996 |
| CA | 2534925 | 2/2005 | EP | 0 696 598 | 2/1996 |
| CA | 2534932 | 2/2005 | EP | 0756480 A1 | 2/1997 |
| CA | 2551231 | 7/2005 | EP | 0760654 A1 | 3/1997 |
| CA | 2572352 | 1/2006 | EP | 0761211 | 3/1997 |
| CA | 2572491 | 1/2006 | EP | 0 780 369 | 6/1997 |
| CA | 2595954 | 7/2006 | EP | 0785775 A1 | 7/1997 |
| CA | 2595979 | 8/2006 | EP | 0820698 | 7/1997 |
| CA | 2713128 | 7/2009 | EP | 0809488 A1 | 12/1997 |
| CA | 2723438 | 11/2009 | EP | 0857062 A2 | 8/1998 |
| CH | 689109 | 10/1998 | EP | 0864324 A1 | 9/1998 |
| CN | 1980643 | 4/2005 | EP | 0864326 A2 | 9/1998 |

| | | | | | | |
|---|---|---|---|---|---|---|
| EP | 0980894 | 2/2000 | | WO | 95 30422 | 11/1995 |
| EP | 0988106 A1 | 3/2000 | | WO | 96 00066 | 1/1996 |
| EP | 1014941 A1 | 7/2000 | | WO | 96/03979 | 2/1996 |
| EP | 1070504 | 1/2001 | | WO | 9614058 A1 | 5/1996 |
| EP | 1127871 | 8/2001 | | WO | 9733566 | 9/1997 |
| EP | 1138321 | 10/2001 | | WO | 9820073 | 5/1998 |
| EP | 1166776 | 1/2002 | | WO | 98/28698 | 7/1998 |
| EP | 1251120 | 10/2002 | | WO | 98/35655 | 8/1998 |
| EP | 1293127 | 3/2003 | | WO | 99/12864 | 3/1999 |
| EP | 1293196 A2 | 3/2003 | | WO | 99 32120 A1 | 7/1999 |
| EP | 1250045 | 9/2003 | | WO | 99/48481 | 9/1999 |
| EP | 1658055 | 2/2005 | | WO | 9944591 | 9/1999 |
| EP | 1515702 | 3/2005 | | WO | 0033835 | 6/2000 |
| EP | 1527775 A1 | 4/2005 | | WO | 0040205 | 7/2000 |
| EP | 1558221 A1 | 8/2005 | | WO | 01/12230 | 2/2001 |
| EP | 1558257 | 8/2005 | | WO | 0108661 | 2/2001 |
| EP | 1560585 | 8/2005 | | WO | 0115667 | 3/2001 |
| EP | 1658054 | 5/2006 | | WO | 01/52651 | 7/2001 |
| EP | 1740161 | 1/2007 | | WO | 01/97783 | 12/2001 |
| EP | 1765303 | 3/2007 | | WO | 02/26061 | 4/2002 |
| EP | 1786403 | 5/2007 | | WO | 02/26262 | 4/2002 |
| EP | 1558221 B1 | 6/2007 | | WO | 02 26928 | 4/2002 |
| EP | 1845955 | 10/2007 | | WO | 02/088217 A1 | 11/2002 |
| EP | 1845956 | 10/2007 | | WO | 03/006723 | 1/2003 |
| EP | 1 859 789 | 11/2007 | | WO | 03 013476 A1 | 1/2003 |
| EP | 1897545 | 12/2008 | | WO | 03/013479 | 2/2003 |
| EP | 2131830 | 12/2009 | | WO | 03 024430 A1 | 2/2003 |
| EP | 2249811 | 11/2010 | | WO | 03015531 | 2/2003 |
| EP | 2273983 | 1/2011 | | WO | 03/026624 A1 | 4/2003 |
| ES | 2336571 | 12/2004 | | WO | 03 028698 A1 | 4/2003 |
| ES | 2260042 | 11/2006 | | WO | 03/028990 A1 | 4/2003 |
| ES | 2285497 | 11/2007 | | WO | 03/031546 | 4/2003 |
| ES | 2288621 | 1/2008 | | WO | 03026743 A2 | 4/2003 |
| ES | 2289542 | 2/2008 | | WO | 03 035029 | 5/2003 |
| ES | 2315505 | 4/2009 | | WO | 03/035177 A2 | 5/2003 |
| GB | 1 147 210 | 4/1969 | | WO | 03035029 | 5/2003 |
| GB | 2057878 | 4/1981 | | WO | 03035053 | 5/2003 |
| HR | P20070272 | 6/2007 | | WO | 03035054 | 5/2003 |
| HR | 20070456 | 11/2007 | | WO | 03053417 | 7/2003 |
| JP | 03-501737 A | 4/1991 | | WO | 03/068392 | 8/2003 |
| JP | 8-505076 A | 6/1996 | | WO | 03/092648 A1 | 11/2003 |
| JP | 2002-275175 | 9/2002 | | WO | 03094812 | 11/2003 |
| JP | 2005534664 | 11/2005 | | WO | 03 105808 | 12/2003 |
| KR | 1020060069832 | 6/2006 | | WO | 2004/004693 A1 | 1/2004 |
| KR | 20070039041 | 4/2007 | | WO | 2004/043967 | 2/2004 |
| KR | 20070111510 | 11/2007 | | WO | 2004 026262 A2 | 4/2004 |
| KR | 20100111303 | 10/2010 | | WO | 2004 026263 A2 | 4/2004 |
| KR | 20110016921 | 2/2011 | | WO | 2004026262 A2 | 4/2004 |
| MX | 2007000008 | 3/2007 | | WO | 2004037230 | 5/2004 |
| MX | 2007000009 | 3/2007 | | WO | 2004037259 | 5/2004 |
| MX | 2007009393 | 8/2007 | | WO | 2004037260 | 5/2004 |
| MX | 2010008138 | 8/2010 | | WO | 2004/066910 A2 | 8/2004 |
| MX | 2010012039 | 11/2010 | | WO | 2004/084869 A1 | 10/2004 |
| NO | 20061054 | 3/2006 | | WO | 2004/093801 A2 | 11/2004 |
| NO | 20070578 | 1/2007 | | WO | 2004/100894 A2 | 11/2004 |
| NO | 20074412 | 11/2007 | | WO | 2004093819 | 11/2004 |
| PT | 1699440 | 12/2004 | | WO | 2005 016313 A1 | 2/2005 |
| PT | 1658054 | 5/2006 | | WO | 2005 016314 | 2/2005 |
| PT | 1658055 | 7/2007 | | WO | 2005016314 | 2/2005 |
| PT | 1515702 | 12/2008 | | WO | 2005/032524 A2 | 4/2005 |
| RU | 2131244 | 6/1999 | | WO | 2005/065646 A2 | 4/2005 |
| RU | 2354357 | 12/2007 | | WO | 2005 041968 | 5/2005 |
| RU | 2007103712 | 9/2008 | | WO | 2005/053587 A1 | 6/2005 |
| RU | 2007103707 | 11/2008 | | WO | 2005/053656 | 6/2005 |
| RU | 2007132975 | 4/2009 | | WO | 2005/055981 A2 | 6/2005 |
| SI | 1515702 | 4/2009 | | WO | 2005 063214 | 7/2005 |
| SI | 1699440 | 11/2009 | | WO | 2005/066183 | 7/2005 |
| WO | 89/05624 | 6/1989 | | WO | 2005063214 | 7/2005 |
| WO | 90 03776 | 4/1990 | | WO | 2005 102286 | 11/2005 |
| WO | 90/03776 A1 | 4/1990 | | WO | 2005102286 | 11/2005 |
| WO | 93 06723 A1 | 4/1993 | | WO | 2005102294 | 11/2005 |
| WO | 93/10758 | 6/1993 | | WO | 2006 002883 | 1/2006 |
| WO | 93 11749 | 6/1993 | | WO | 2006 002884 | 1/2006 |
| WO | 93 23017 | 11/1993 | | WO | 2006/002886 | 1/2006 |
| WO | 94 06414 | 3/1994 | | WO | 2006002884 | 1/2006 |
| WO | 94/08567 | 4/1994 | | WO | 2006 082097 | 8/2006 |
| WO | 95/17174 | 6/1995 | | WO | 2006 082099 | 8/2006 |
| WO | 95/22319 | 8/1995 | | WO | 2007/005716 A2 | 1/2007 |
| WO | 9520947 | 8/1995 | | WO | 2007 008752 | 1/2007 |

| | | |
|---|---|---|
| WO | 2007 048233 | 5/2007 |
| WO | 2007 053698 | 5/2007 |
| WO | 2007/085024 A2 | 7/2007 |
| WO | 2008/086804 | 7/2008 |
| WO | 2008/107149 | 9/2008 |
| WO | 2008107149 | 9/2008 |
| WO | 2008/148798 | 11/2008 |
| WO | 2009/092601 A1 | 7/2009 |
| WO | 2009092601 | 7/2009 |
| WO | 2009/135680 A1 | 11/2009 |
| WO | 2009135680 | 11/2009 |
| WO | 2011009602 | 1/2011 |
| WO | 2011009603 | 1/2011 |
| WO | 2011009604 | 1/2011 |

OTHER PUBLICATIONS

F. E. Bailey et al., "Some Properties of Poly(ethylene oxide)' in Aqueous Solution," Journal of Applied Polymer Science, vol. 1, Issue No. 1, pp. 56-62 (1959).

A. Apicella et al., "Poly(ethylene oxide) (PEO) and different molecular weight PEO blends monolithic devices for drug release," Biomaterials 1993, vol. 14, No. 2, pp. 83-90.

S. Janicki et al., "Slow-Release Microballs: Method of Preparation," Acta Pharm. Technol. 33(3) 154-155 (1987).

R. Mank et al., "Darstellung wirkstoffhaltiger Extrusionsformlinge auf der Basis von Thermoplasten," Pharmazie 45 (1990), H. 8; pp. 592-593.

R. Mank et al., "Darstellung wirkstoffhaltiger Extrusionsformlinge auf der Basis von Thermoplasten," Pharmazie 44 (1989) H. 11; pp. 773-776.

P. Shivanand et al., "Factors Affecting Release of KCl from Melt Extruded Polyethylene Disks," Pharmaceutical Research, Official Journal of the American Association of Pharmaceutical Scientists; Oct. 1991, vol. 8, No. 10.

L. Yang et al., "Characterization of Compressibility and Compatibility of Poly(ethylene oxide) Polymers for Modified Release Application by Compaction Simulator," Journal of Pharmaceutical Sciences, vol. 85, No. 10, Oct. 1996.

F. Zhang et al., "Properties of Sustained-Release Tablets Prepared by Hot-Melt Extrusion," Pharmaceutical Development and Technology, 4(2), 241-250 (1999) pp. 241-250.

M.M. Crowley et al., "Stability of polyethylene oxide in matrix tablets prepared by hot-melt extrusion," Biomaterials 23 (2002) 4241-4248.

M. Efentakis et al., "Evaluation of High Molecular Weight Poly(Oxyethylene) (Polyox) Polymer: Studies of Flow Properties and Release Rates of Furosemide and Captopril from Controlled-Release Hard Gelatin Capsules," Pharmaceutical Development and Technology, 5(3), 339-346 (2000).

N. Follonier et al., "Various ways of modulating the release of diltiazem hydrochloride from hot-melt extruded sustained release pellets prepared using polymeric materials," Journal of Controlled Release 36 (1995) 243-250.

N.B. Graham, "Poly(Ethylene Glycol) Gels and Drug Delivery," Poly(Ethylene Glycol) Chemistry: Biotechnical and Biomedical Applications, Chapter 17, 1992.

C. D. Hanning et al., "The Morphine Hydrogel Suppository," British Journal of Anaesthesia, 1988, 61, 221-227.

Kim et al., "Preparation and Evaluation of Eudragit Gels V. Rectal Gel Preparations for Sustained Release and Avoidance of First-Pass Metabolism of Lidocaine," Chem. Pharm. Bull. 40(10) 2800-2804 (1992).

Cherng-Ju Kim, "Drug Release from Compressed Hydrophilic POLYOX-WSR Tablets," Journal of Pharmaceutical Sciences, vol. 84, No. 3, Mar. 1995.

S.L. Madorsky et al., "Thermal Degradation of Polyethylene Oxide and Polypropylene Oxide," Journal of Polymer Science, vol. XXXVI, pp. 183-194 (1959).

A. Moroni et al., "Application of Poly(Oxyethylene) Homopolymers in Sustained Release Solid Formulations," Drug Development and Industrial Pharmacy, 21(12), 1411-1428 (1995).

N. Ohnishi et al., "Effect of the Molecular Weight of Polyethylene Glycol on the Bioavailability of Indomethacin Sustained-Release Suppositories Prepared with Solid Dispersions," Chem. Pharm. Bull., 35 (8) 3511-3515 (1987).

T. Ozeki et al., "Control of medicine release from solid dispersion composed of the poly(ethylene oxide)-carboxyvinylpolymer interpolymer complex by varying molecular weight of poly(ethylene oxide)," Journal of Controlled Release 58 (1999) 87-95.

Pharmaceutical Research, Official Journal of the American Association of Pharmaceutical Scientists, Sep. 1989 (Supplement), vol. 6, No. 9, 6.S-98.

Pharmaceutical Research, Official Journal of the American Association of Pharmaceutical Scientists, Oct. 1991 (Supplement), Vo. 8, No. 10, 8.S-192.

W. Prapaitrakul et al., "Release of Chlorpheniramine Maleate from Fatty Acid Ester Matrix Disks Prepared by Melt-extrusion," J. Pharm. Pharmacol. 1991, 43: 377-381.

S. Radko et al., "Molecular sieving by polymer solutions: dependence on particle and polymer size, independence of polymer entanglement," Applied and Theoretical Electrophoresis (1995), 5, 79-88.

J. Scheirs et al., "Characterizing the solid-state thermal oxidation of poly(ethylene oxide) powder," Polymer, 1991, vol. 32, No. 11.

O.L. Sprockel et al., "Permeability of Cellulose Polymers: Water Vapour Transmission Rates," J. Pharm. Pharmacol. 1990, 42: 152-157.

J.L. Stringer et al., "Diffusion of small molecular weight drugs in radiation-crosslinked poly(ethylene oxide) hydrogels," Journal of Controlled Release 42 (1996) 195-202.

E. G. Rippie et al., "Regulation of Dissolution Rate by Pellet Geometry," Journal of Pharmaceutical Sciences, Vo. 58, No. 4, Apr. 1969, pp. 428-431.

M. Adel El-Egakey et al., "Hot extruded dosage forms Part I," Pharmaceutica Acta Helvetiae, vol. 46, Mar. 19, 1970.

Remington's Pharmaceutical Sciences 17th ed., Mack Publishing Co., (1985) 1418.

M.S. Mesiha et al., "A Screening Study of Lubricants in Wet Powder Masses Suitable for Extrusion Spheronization," Drug Development and Industrial Pharmacy, 19(8), 943-959 (1993).

N. Follonier et al., "Evaluation of Hot-Melt Extrusion as a New Technique for the Production of Polymer-Based Pellets for Sustained Release Capsules Containing High Loadings of Freely Soluble Drugs," Drug Development and Industrial Pharmacy, 20(8), 1323-1339 (1994).

Coppens et al; "Hypromellose, Ethylcellulose, and Polyethylene Oxide Use in Hot Melt Extrusion"; Pharmaceutical Technology, 62-70, Jan. 2005.

Proeschel, et al, J. Dent. Res. 81(7), 2002, pp. 464-468.

Schroder, J. Granulierung hydrophober Wirkstoffe, vol. 65, No. 4, 2003, pp. 367-372.

Remington's Pharmaceutical Sciences, Authur Asol editor, pp. 1553-1593, Chapter 89, 1980.

Inert Gas from Wikipedia (Dec. 2009).

Observations by Third Parties Pursuant to Art 115 EPC, dated Feb. 2, 2009.

Letter of James W. McGinity, with attached experimental report, dated Jan. 26, 2009.

Bauer, Kurt J., et al; "Coated Pharmaceutical Dosage Forms, Fundamentals, Manufacturing Techniques, Biopharmaceutical Aspects, Test Methods and Raw Materials"; Scientific Publishers, Stuttgart, 1998.

"Pharmaceutical technical procedures"; European Pharmacopofia, 1997, p. 135.

Granuilerung hydrophober wirkstoffe im planetuxlzenextruder (2003).

Maggie et al; Biomaterials (2002), 23, pp. 1113-1119.

Braun, et al., "S study of bite force, part 2: Relationship . . . ", 1995, Angel Orthodontist, 6(5), pp. 373-377.

DeJong (Pharmaceutisch Weekblad Scientific Edition 1987, p. 24-28).

Dow Excipients Chem. of Poly. Water Soluble-Resin 2004, pp. 1-2.

Tipler, et al, Physics for Scientists and Engineers, 6th Edition, pp. 234-235, 2003.

Stafford J., überzogene feste Formen, 1991, 347-68.
Jan. 6, 2011 Letter from Dr. Rick Matos, Ph.D.
Caraballo, Journal of Controlled Release, vol. 69, pp. 345-355, 2000.
DOW Technical Data, POLYOX, Feb. 2003.
Davies, et al; European Journal of Pharmaceutics and Biopharmaceutics, 67, 2007, pp. 268-276.
El-Sherbiny, European Polymer Journal, vol. 41, pp. 2584-2591, 2005.
Fell, et al, Journal of Pharmaceutical Sciences, vol. 59, No. 5, May 1970, pp. 688-691.
Griffith, Drug Administration, vol. 19, No. 1, pp. 41-42, 2003.
Levina, Journal of Pharmaceutical Sciences, vol. 89, No. 6, pp. 703-723, Jun. 2000.
Levina, Drug Development and Industrial Pharmacy, vol. 28, No. 5, pp. 495-514, 2002.
Lockhart et al, "Packaging of Pharmaceuticals and Health Care Products"; Blackie Academic & Professional; First Edition 1996.
Miller, Nursing, pp. 50-52, Feb. 2000.
Mitchell, Special Resource, vol. 35, No. 5, pp. 535-557, 2000.
Varma, Manthena et al, Am. J. Drug Deliv. 2004: 2 (1): 43-57.
Summers et al; Journal of Pharmaceutical Sciences, vol. 66, No. 8, Aug. 1977, pp. 1172-1175.
US Pharmacopoeia, Chapter 1217, Aug. 1, 2008.
Yarbrough et al, Letters to Nature 322, 347-349 (Jul. 24, 1986) "Extraordinary effects of mortar-and-pestle grinding on microstructure of sintered alumina gel".
Maggi. Therapeutic Potential of Capsaicin-like Molecules. 1Life Sciences, vol. 51, pp. 1777-1781, 1992.
Maggi, L. et al., "High molecular weight polyethylene oxides (PEOs) as an alternative to HPMC in controlled release dosage form", 2000, International Journal of Pharmaceutics, 195 pp. 229-238.
Freed et al. pH control of nucleophilic/electrophilic oxidation. International Journal of Pharmaceutics. 2008, vol. 357, pp. 180-188.
Waterman et al. Stabilization of Pharmaceuticals to Oxidative Degradation. Pharmaceutical Development and Technology. 2002, vol. 7, No. 1, pp. 1-32.
Handbuch der Kunststoff-Extrusionstechnik 1, "Grundlagen" in Chapter 1.2 "Klassifizierung von Extrudern", pp. 3-7. 1989.
2.9 Methoden der pharmazeutischen Technologie 143-144, 1997.
Conversion of 18.8 kiloponds to newtons, http://www.unitconversion.org/force/newtons-to-kiloponds-conversion.html on Jul. 5, 2011.
Waltimo et al. A novel bite force recorder and maximal isometric bite force values for healthy young adults. Scand J Dent Res. 1993, vol. 101, pp. 171-175.
Waltimo et al. Maximal bite force and its association with signs and symptoms of crandiomandibular disorders in young Finnish non-patients. Acta Odonol. Scand. 1995, vol. 53, pp. 254-258.
Katz et al., Clin. J. Pain, 23(8): 648-660 (2007).
Arnold, "Teen Abuse of Painkiller OxyContin on the Rise," www.npr.org, Dec. 19, 2005.
Baum et al., Public Health Reports, 102(4): 426-429 (1987).
Purdue News, "Purdue Pharma Provides Update on Development of New Abuse-Resistant Pain Medications; FDA Cites Patient Needs As First Priority; New Drug Application Delayed," www.headaches.about.com, Jun. 18, 2002.
Strang, British Med. J., 302: 969 (1991).
Tompkins et al., Psychopharma., 210: 471-480 (2010).
Waters et al., Am. J. Psychiatry, 164(1): pp. 173-174 (2007).
Tablet, www.docstoc.com (2011).
Dachille, F. et al., "High-Pressure Phase Transformation in Laboratory Mechanical Mixers and Mortars", 1960, Nature, 186, pp. 1-2 (abstract).
Stafford J. Uberzogene feste Formen, 1991, pp. 347-368.
Remington's Pharmaceutical Sciences, Ch. 76, 1985, 17th Edition.
Remington's Pharmaceutical Sciences, Ch. 77, 1985, 17th Edition.
Remington's Pharmaceutical Sciences, Ch. 78, 1985, 17th Edition.
Remington's Pharmaceutical Sciences, Ch. 79, 1985, 17th Edition.
Remington's Pharmaceutical Sciences, Ch. 80, 1985, 17th Edition.
Remington's Pharmaceutical Sciences, Ch. 81, 1985, 17th Edition.
Remington's Pharmaceutical Sciences, Ch. 82, 1985, 17th Edition.
Remington's Pharmaceutical Sciences, Ch. 83, 1985, 17th Edition.
Remington's Pharmaceutical Sciences, Ch. 84, 1985, 17th Edition.
Remington's Pharmaceutical Sciences, Ch. 85, 1985, 17th Edition.
Remington's Pharmaceutical Sciences, Ch. 86, 1985, 17th Edition.
Remington's Pharmaceutical Sciences, Ch. 87, 1985, 17th Edition.
Remington's Pharmaceutical Sciences, Ch. 88, 1985, 17th Edition.
Remington's Pharmaceutical Sciences, Ch. 89, 1985, 17th Edition.
Remington's Pharmaceutical Sciences, Ch. 91, 1985, 17th Edition.
Remington's Pharmaceutical Sciences, Ch. 92, 1985, 17th Edition.
Remington's Pharmaceutical Sciences, Ch. 93, 1985, 17th Edition.
Wu et al. Mathematical modeling and in vitro study of controlled drug release via a highly swellable and dissoluble polymer matrix: polyethylene oxide with high molecular weights. Journal of Controlled Release. 2005. vol. 102, pp. 569-581.
Remington's Pharmaceutical Sciences, Ch. 90, 1985, 17th Edition.

ABUSE-PROOF DOSAGE FORM

CROSS REFERENCE TO RELATED APPLICATIONS

This application is a division of U.S. Ser. No. 11/462,216, filed Aug. 3, 2006, now pending, which is, in turn, a continuation-in-part of U.S. Ser. No. 11/349,544, filed Feb. 6, 2006, and a continuation-in-part of U.S. Ser. No. 11/348,295, filed Feb. 6, 2006, and a continuation-in-part of U.S. Ser. No. 10/718,112, filed Nov. 20, 2003, and also claims priority of German Patent Application No. 10 2005 005446.3 filed on Feb. 4, 2005, and German Patent Application No. 10 336 400.5, filed on Aug. 6, 2003.

BACKGROUND OF THE INVENTION

The present invention relates to an abuse-proofed dosage form thermoformed by extrusion without discoloration and containing, in addition to one or more active ingredients with abuse potential (A) optionally together with physiologically acceptable auxiliary substances (B), at least one synthetic or natural polymer (C) and optionally at least one wax (D), wherein the dosage form exhibits a breaking strength (=resistance to crushing) of at least 500 N, and to a process for the production of the dosage form according to the invention.

Many pharmaceutical active ingredients, in addition to having excellent activity in their appropriate application, also have abuse potential, i.e. they can be used by an abuser to bring about effects other than those intended. Opiates, for example, which are highly active in combating severe to very severe pain, are frequently used by abusers to induce a state of narcosis or euphoria.

In order to make abuse possible, the corresponding dosage forms, such as tablets or capsules are comminuted, for example ground in a mortar, by the abuser, the active ingredient is extracted from the resultant powder using a preferably aqueous liquid and the resultant solution, optionally after being filtered through cotton wool or cellulose wadding, is administered parenterally, in particular intravenously. An additional phenomenon of this kind of administration, in comparison with abusive oral administration, is a further accelerated increase in active ingredient levels giving the abuser the desired effect, namely the "kick" or "rush". This kick is also obtained if the powdered dosage form is administered nasally, i.e. is sniffed. Since controlled-release dosage forms containing active ingredients with abuse potential do not give rise to the kick desired by the abuser when taken orally even in abusively high quantities, such dosage forms are also comminuted and extracted in order to be abused.

U.S. Pat. No. 4,070,494 proposed adding a swellable agent to the dosage form in order to prevent abuse. When water is added to extract the active ingredient, this agent swells and ensures that the filtrate separated from the gel contains only a small quantity of active ingredient.

The multilayer tablet disclosed in WO 95/20947 is based on a similar approach to preventing parenteral abuse, said tablet containing the active ingredient with abuse potential and at least one gel former, each in different layers.

WO 03/015531 A2 discloses another approach to preventing parenteral abuse. A dosage form containing an analgesic opioid and a dye as an aversive agent is described therein. The color released by tampering with the dosage form is intended to discourage the abuser from using the dosage form which has been tampered with.

Another known option for complicating abuse involves adding antagonists to the active ingredients to the dosage form, for example naloxone or naltexone in the case of opioids, or compounds which cause a physiological defense response, such as for example ipecacuanha (ipecac) root.

However, since in most cases of abuse it is still necessary to pulverize the dosage form comprising an active ingredient suitable for abuse, it is an object of the present invention to complicate or prevent the pulverization preceding abuse of the dosage form using the means conventionally available to a potential abuser.

It is a further object to provide a dosage form for active ingredients with potential for abuse which ensures the desired therapeutic effect when correctly administered, but from which the active ingredients cannot be converted into a form suitable for abuse simply by pulverization.

An additional object is to provide a dosage form with enhanced stability when maintained under adverse conditions.

Yet another object is to provide an extrusion process for the manufacture of dosage forms having enhanced abuse prevention and stability characteristics.

A further object is to provide a dosage form having a surface morphology different from that of the core of the dosage form.

An additional object is to provide a dosage form having a non-uniform morphology in general and in particular a dosage form having a layered morphology, in each case where the composition of the dosage form remains uniform.

SUMMARY OF THE INVENTION

These objects have been achieved by the provision of the abuse-proofed dosage form thermoformed by extrusion without discoloration according to the invention which contains, in addition to one or more active ingredients with abuse potential (A), at least one synthetic or natural polymer (C) optionally at least one wax (D), and optionally at least one physiologically acceptable auxiliary substance (B), wherein the dosage form exhibits a breaking strength of at least 500 N.

The breaking strength of at least 500 N (measured as stated in the specification) means that pulverization of the dosage form is considerably more difficult using conventional means, so considerably complicating or preventing the subsequent abuse.

If comminution is inadequate, parenteral, in particular intravenous, administration cannot be performed safely or extraction of the active ingredient therefrom takes too long for the abuser or there is no "kick" when taken orally, as release is not instantaneous.

As used herein, comminution means pulverization of the dosage form with conventional means which are available to an abuser, such as, for example, a mortar and pestle, a hammer, a mallet or other usual means for pulverization by application of force.

The dosage form according to the invention is thus suitable for preventing parenteral, nasal and/or oral abuse of active ingredients, preferably of pharmaceutical active ingredients, with abuse potential.

The advantageous properties of the dosage form according to the invention, in particular also its mechanical properties, may not automatically be achieved by simply processing components (A), (C), optionally (B) and optionally (D) by means of conventional methods for the preparation of dosage forms. In fact, usually suitable apparatuses must be selected for the preparation and critical processing parameters must be adjusted, particularly pressure/force, temperature and time. Dosage forms exhibiting the desired properties may be obtained only if in the course of the preparation of the dosage form the components are exposed to a sufficient pressure at a sufficient temperature for a sufficient period of time. Thus, although it may be possible to utilize conventional apparatuses, the process protocols usually must be adapted in order to meet the required criteria.

Unlike prior art methods which involve the extrusion of polymers in admixture with pharmaceutically active substances but which fail to provide the dosage forms with the beneficial characteristics according to the present invention because unsuitable extruder types are chosen and/or improper extrusion parameters are adjusted, it has now been discovered that the combination of specific extruder type coupled with herein specified extrusion process parameters provides dosage forms with the enhanced properties disclosed herein.

For example, U.S. Pat. No. 6,488,963 relates to pharmaceutical formulations comprising a hot-melt extrudable mixture of a therapeutic compound and a high molecular weight poly(ethylene oxide). It is disclosed that any commercially available extruder model equipped to handle dry feed and having a solid conveying zone, one or multiple heating zones, and an extrusion die may be used. A single screw extruder is preferred and used in the examples. Besides hot-melt extrusion, other equivalent processes such as injection molding, hot dipping, melt casting and compression molding are said to be useful. The pharmaceutical formulations obtained by the extrusion process according to U.S. Pat. No. 6,488,963, however, fundamentally differ from the dosage forms according to the present invention. This becomes directly evident from the further processing of the extrudate of Example 2 of U.S. Pat. No. 6,488,963, which, upon exiting the die, may be chopped to the desired length and then be ground to a powder. According to U.S. Pat. No. 6,488,963, such powders are preferred for oral, buccal, and sublingual administration.

In contrast to the grindable pharmaceutical formulations according to U.S. Pat. No. 6,488,963, it is an essential feature of the dosage forms according to the present invention that they exhibit a breaking strength of at least 500 N thereby preventing them from being ground to a powder. In the preparation of the dosage forms according to the invention, a suitable extruder type has to be chosen and the extrusion parameters have to be properly adjusted in order to achieve a breaking strength of at least 500 N. In general, single screw extruders of the type disclosed in U.S. Pat. No. 6,488,963 are not suitable to produce the dosage forms according to the present invention.

DETAILED DESCRIPTION OF THE INVENTION

Figure 1:
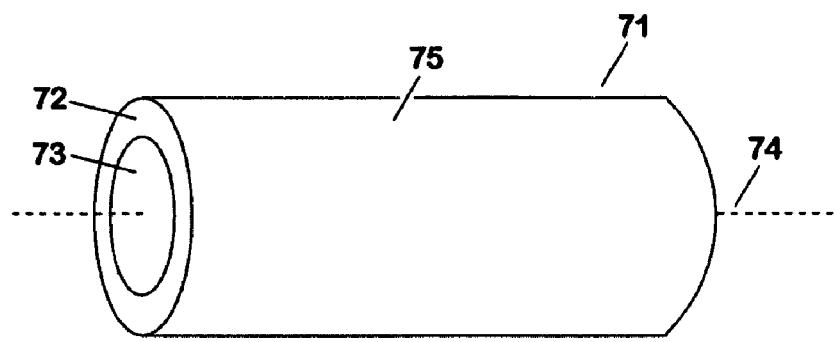
FIG. 1 shows a schematic view of the extrudate of the composition.

Pharmaceutical active ingredients with abuse potential are known to the person skilled in the art, as are the quantities thereof to be used and processes for the production thereof, and may be present in the dosage form according to the invention as such, in the form of the corresponding derivatives thereof, in particular esters or ethers, or in each case in the form of corresponding physiologically acceptable compounds, in particular in the form of the salts or solvates thereof, as racemates or stereoisomers. The dosage form according to the invention is also suitable for the administration of two or more pharmaceutical active ingredients in one dosage form. The dosage form preferably contains just one specific active ingredient.

The dosage form according to the invention is in particular suitable for preventing abuse of a pharmaceutical active ingredient selected from the group consisting of opioids, tranquillizers, preferably benzodiazepines, barbiturates, stimulants and other narcotics.

The dosage form according to the invention is very particularly suitable for preventing abuse of an opioid, tranquillizer or another narcotic selected from the group consisting of N-{1-[2-(4-ethyl-5-oxo-2-tetrazolin-1-yl)ethyl]-4-methoxymethyl-4-piperidyl}propionanilide (alfentanil), 5,5-diallylbarbituric acid (allobarbital), allylprodine, alphaprodine, 8-chloro-1-methyl-6-phenyl-4H-[1,2,4]triazolo[4,3-a][1,4]-benzodiazepine (alprazolam), 2-diethylaminopropiophenone (amfepramone), (±)-α-methylphenethylamine (amphetamine), 2-(α-methylphenethylamino)-2-phenylacetonitrile (amphetaminil), 5-ethyl-5-isopentylbarbituric acid (amobarbital), anileridine, apocodeine, 5,5-diethylbarbituric acid (barbital), benzylmorphine, bezitramide, 7-bromo-5-(2-pyridyl)-1H-1,4-benzodiazepine-2(3H)-one (bromazepam), 2-bromo-4-(2-chlorophenyl)-9-methyl-6H-thieno[3,2-f][1,2,4]triazolo-[4,3-a][1,4]diazepine (brotizolam), 17-cyclopropylmethyl-4,5a-epoxy-7α[(S)-1-hydroxy-1,2,2-trimethyl-propyl]-6-methoxy-6,14-endo-ethanomorphinan-3-ol (buprenorphine), 5-butyl-5-ethylbarbituric acid (butobarbital), butorphanol, (7-chloro-1,3-dihydro-1-methyl-2-oxo-5-phenyl-2H-1,4-benzodiazepin-3-yl) dimethylcarbamate (camazepam), (1S,2S)-2-amino-1-phenyl-1-propanol (cathine/D-norpseudoephedrine), 7-chloro-N-methyl-5-phenyl-3H-1,4-benzodiazepin-2-ylamine 4-oxide (chlordiazepoxide), 7-chloro-1-methyl-5-phenyl-1H-1,5-benzodiazepine-2,4(3H,5H)-dione (clobazam), 5-(2-chlorophenyl)-7-nitro-1H-1,4-benzodiazepin-2(3H)-one (clonazepam), clonitazene, 7-chloro-2,3-dihydro-2-oxo-5-phenyl-1H-1,4-benzodiazepine-3-carboxylic acid (clorazepate), 5-(2-chlorophenyl)-7-ethyl-1-methyl-1H-thieno[2,3-e][1,4]diazepin-2(3H)-one (clotiazepam), 10-chloro-11β-(2-chlorophenyl)-2,3,7,11β-tetrahydrooxazolo[3,2-d][1,4]benzodiazepin-6 (5H)-one (cloxazolam), (−)-methyl-[3β-benzoyloxy-2β (1αH,5αH)-tropancarboxylate] (cocaine), 4,5α-epoxy-3-methoxy-17-methyl-7-morphinan-6α-ol (codeine), 5-(1-cyclohexenyl)-5-ethylbarbituric acid (cyclobarbital), cyclorphan, cyprenorphine, 7-chloro-5-(2-chlorophenyl)-1H-1,4-benzodiazepin-2(3H)-one (delorazepam), desomorphine, dextromoramide, (+)-(1-benzyl-3-dimethylamino-2-methyl-1-phenylpropyl)propionate (dextropropoxyphen), dezocine, diampromide, diamorphone, 7-chloro-1-methyl-5-phenyl-1H-1,4-benzodiazepin-2(3H)-one (diazepam), 4,5α-epoxy-3-methoxy-17-methyl-6α-morphinanol (dihydrocodeine), 4,5α-epoxy-17-methyl-3,6α-morphinandiol (dihydromorphine), dimenoxadol, dimepheptanol, dimethylthiambutene, dioxaphetyl butyrate, dipipanone, (6αR, 10αR)-6,6,9-trimethyl-3-pentyl-6α,7,8,10α-tetrahydro-6H-benzo[c]chromen-1-ol (dronabinol), eptazocine, 8-chloro-6-phenyl-4H-[1,2,4]triazolo[4,3-a][1,4]benzodiazepine (estazolam), ethoheptazine, ethylmethylthiambutene, ethyl [7-chloro-5-(2-fluorophenyl)-2,3-dihydro-2-oxo-1H-1,4-benzodiazepine-3-carboxylate] (ethyl loflazepate), 4,5α-epoxy-3-ethoxy-17-methyl-7-morphinen-6α-ol (ethylmorphine), etonitazene, 4,5α-epoxy-7α-(1-hydroxy-1-methylbutyl)-6-methoxy-17-methyl-6,14-endo-etheno-morphinan-3-ol (etorphine), N-ethyl-3-phenyl-8,9,10-trinorbornan-2-ylamine (fencamfamine), 7-[2-(α-methylphenethylamino)ethyl]-theophylline) (fenethylline), 3-(α-methylphenethylamino)propionitrile (fenproporex), N-(1-phenethyl-4-piperidyl)propionanilide (fentanyl), 7-chloro-5-(2-fluorophenyl)-1-methyl-1H-1,4-benzodiazepin-2(3H)-one (fludiazepam), 5-(2-fluorophenyl)-1-methyl-7-nitro-1H-1,4-benzodiazepin-2(3H)-one (flunitrazepam), 7-chloro-1-(2-diethylaminoethyl)-5-(2-fluorophenyl)-1H-1,4-benzodiazepin-2(3H)-one (flurazepam), 7-chloro-5-phenyl-1-(2,2,2-trifluoroethyl)-1H-1,4-benzodiazepin-2(3H)-one (halazepam), 10-bromo-11β-(2-fluorophenyl)-2,3,7,11β-tetrahydro[1,3]oxazolyl[3,2-d][1,4]benzodiazepin-6(5H)-one (haloxazolam), heroin, 4,5α-epoxy-3-methoxy-17-methyl-6-morphinanone (hydrocodone), 4,5α-epoxy-3-hydroxy-17-methyl-6-morphinanone (hydromorphone), hydroxypethidine, isomethadone, hydroxymethyl morphinane, 11-chloro-8,12β-dihydro-2,8-dimethyl-12β-phenyl-4H-[1,3]oxazino[3,2-d][1,4]benzodiazepine-4,7(6H)-dione (ketazolam), 1-[4-(3-hydroxyphenyl)-1-methyl-4-piperidyl]-1-propanone (ketobemidone), (3S,6S)-6-dimethylamino-4,4-diphenylheptan-3-yl acetate (levacetylmethadol (LAAM)), (−)-6-dimethylamino-4,4-diphenol-3-heptanone (levomethadone), (−)-17-methyl-3-morphinanol (levorphanol), levophenacylmorphane, lofentanil, 6-(2-chlorophenyl)-2-(4-methyl-1-piperazinylmethylene)-8-nitro-2H-imidazo[1,2-a][1,4]-benzodiazepin-1(4H)-one (loprazolam), 7-chloro-5-(2-chlorophenyl)-3-hydroxy-1H-1,4-benzodiazepin-2(3H)-one (lorazepam), 7-chloro-5-(2-chlorophenyl)-3-hydroxy-1-methyl-1H-1,4-benzodiazepin-2(3H)-one (lormetazepam), 5-(4-chlorophenyl)-2,5-dihydro-3H-imidazo[2,1-a]isoindol-5-ol (mazindol), 7-chloro-2,3-dihydro-1-methyl-5-phenyl-1H-1,4-benzodiazepine (medazepam), N-(3-chloropropyl)-α-methylphenethylamine (mefenorex), meperidine, 2-methyl-2-propyltrimethylene dicarbamate (meprobamate), meptazinol, metazocine, methylmorphine, N,α-dimethylphenethylamine (methamphetamine), (±)-6-dimethylamino-4,4-diphenyl-3-heptanone (methadone), 2-methyl-3-o-tolyl-4(3H)-quinazolinone (methaqualone), methyl[2-phenyl-2-(2-piperidyl)acetate] (methylphenidate), 5-ethyl-1-methyl-5-phenylbarbituric acid (methylphenobarbital), 3,3-diethyl-5-methyl-2,4-piperidinedione (methyprylon), metopon, 8-chloro-6-(2-fluorophenyl)-1-methyl-4H-imidazo[1,5-a][1,4]benzodiazepine (midazolam), 2-(benzhydrylsulfinyl)acetamide (modafinil), 4,5α-epoxy-17-methyl-7-morphinan-3,6α-diol (morphine), myrophine, (±)-trans-3-(1,1-dimethylheptyl)-7,8,10,10α-tetrahydro-1-hydroxy-6,6-dimethyl-6H-dibenzo[-b,d]pyran-9(6αH)-one (nabilone), nalbuphine, nalorphine, narceine, nicomorphine, 1-methyl-7-nitro-5-phenyl-1H-1,4-benzodiazepin-2(3H)-one (nimetazepam), 7-nitro-5-phenyl-1H-1,4-benzodiazepin-2(3H)-one (nitrazepam), 7-chloro-5-phenyl-1H-1,4-benzodiazepin-2(3H)-one (nordazepam), norlevorphanol, 6-dimethylamino-4,4-diphenyl-3-hexanone (normethadone), normorphine, norpipanone, the exudation for the plants belonging to the species Papaver somniferum (opium), 7-chloro-3-hydroxy-5-phenyl-1H-1,4-benzodiazepin-2(3H)-one (oxazepam), (cis-trans)-10-chloro-2,3,7,11b-tetrahydro-2-methyl-11b-phenyloxazolo[3,2-d][1,4]benzodiazepin-6-(5H)-one (oxazolam), 4,5α-epoxy-14-hydroxy-3-methoxy-17-methyl-6-morphinanone (oxycodone), oxymorphone, plants and parts of plants belonging to the species Papaver somniferum (including the subspecies setigerum), papaveretum, 2-imino-5-phenyl-4-oxazolidinone (pernoline), 1,2,3,4,5,6-hexahydro-6,11-dimethyl-3-(3-methyl-2-butenyl)-2,6-methano-3-benzazocin-8-ol (pentazocine), 5-ethyl-5-(1-methylbutyl)-barbituric acid (pentobarbital), ethyl (1-methyl-4-phenyl-4-piperidine carboxylate) (pethidine), phenadoxone, phenomorphan, phenazocine, phenoperidine, piminodine, pholcodine, 3-methyl-2-phenylmorpholine (phenmetrazine), 5-ethyl-5-phenylbarbituric acid (phenobarbital), α,α-dimethylphenethylamine (phentermine), 7-chloro-5-phenyl-1-(2-propynyl)-1H-1,4-benzodiazepin-2(3H)-one (pinazepam), α-(2-piperidyl)benzhydryl alcohol (pipradrol), 1'-(3-cyano-3,3-diphenylpropyl)[1,4'-bipiperidine]-4'-carboxamide (piritramide), 7-chloro-1-(cyclopropylmethyl)-5-phenyl-1H-1,4-benzodiazepin-2(3H)-one (prazepam), profadol, proheptazine, promedol, properidine, propoxyphene, N-(1-methyl-2-piperidinoethyl)-N-(2-pyridyl)propionamide, methyl {3-[4-methoxycarbonyl-4-(N-phenylpropanamido)-piperidino]propanoate} (remifentanil), 5-sec-butyl-5-ethylbarbituric acid (secbutabarbital), 5-allyl-5-(1-methylbutyl)-barbituric acid (secobarbital), N-{4-methoxymethyl-1-[2-(2-thienyl)ethyl]-4-piperidyl}-propionanilide (sufentanil), 7-chloro-2-hydroxy-methyl-5-phenyl-1H-1,4-benzodiazepin-2(3H)-one (temazepam), 7-chloro-5-(1-cyclohexenyl)-1-methyl-1H-1,4-benzodiazepin-2(3H)-one (tetrazepam), ethyl (2-dimethylamino-1-phenyl-3-cyclohexene-1-carboxylate) (tilidine (cis and trans)), tramadol, 8-chloro-6-(2-chlorophenyl)-1-methyl-4H-[1,2,4]triazolo[4,3-a][1,4]benzodiazepine (triazolam), 5-(1-methylbutyl)-5-vinylbarbituric acid (vinylbital), (1R,2R)-3-(3-dimethylamino-1-ethyl-2-methyl-propyl)-phenol, (1R,2R,4S)-2-(dimethylamino)methyl-4-(p-fluorobenzyloxy)-1-(m-methoxyphenyl)cyclohexanol, (1R,2R)-3-(2-dimethylaminomethyl-cyclohexyl)phenol, (1S,2S)-3-(3-dimethylamino-1-ethyl-2-methyl-propyl)phenol, (2R,3R)-1-dimethylamino-3-(3-methoxyphenyl)-2-methyl-pentan-3-ol, (1RS,3RS,6RS)-6-dimethylaminomethyl-1-(3-methoxyphenyl)-cyclohexan-1,3-diol, preferably as racemate, 3-(2-dimethylaminomethyl-1-hydroxy-cyclohexyl)phenyl 2-(4-isobutylphenyl)-propionate, 3-(2-dimethylaminomethyl-1-hydroxycyclohexyl)phenyl 2-(6-methoxy-naphthalen-2-yl)-propionate, 3-(2-dimethylaminomethyl-cyclohex-1-enyl)-phenyl 2-(4-isobutylphenyl)-propionate, 3-(2-dimethylaminomethyl-cyclohex-1-enyl)-phenyl 2-(6-methoxy-naphthalen-2-yl)-propionate, (RR—SS)-2-acetoxy-4-trifluoromethyl-benzoic acid 3-(2-dimethylaminomethyl-1-hydroxy-cyclohexyl)-phenyl ester, (RR—SS)-2-hydroxy-4-trifluoromethyl-benzoic acid 3-(2-dimethylaminomethyl-1-hydroxy-cyclohexyl)-phenyl ester, (RR—SS)-4-chloro-2-hydroxybenzoic acid 3-(2-dimethylaminomethyl-1-hydroxy-cyclohexyl)-phenyl ester, (RR—SS)-2-hydroxy-4-methyl-benzoic acid 3-(2-dimethylaminomethyl-1-hydroxy-cyclohexyl)-phenyl ester, (RR—SS)-2-hydroxy-4-methoxy-benzoic acid 3-(2-dimethylaminomethyl-1-hydroxy-cyclohexyl)-phenyl ester, (RR—SS)-2-hydroxy-5-nitrobenzoic acid 3-(2-dimethylaminomethyl-1-hydroxy-cyclohexyl)-phenyl ester, (RR—SS)-2',4'-difluoro-3-hydroxy-biphenyl-4-carboxylic acid 3-(2-dimethylaminomethyl-1-hydroxycyclohexyl)-phenyl ester and corresponding stereoisomeric compounds, the corresponding derivatives thereof in each case, in particular amides, esters or ethers, and the physiologically acceptable compounds thereof in each case, in particular the salts and solvates thereof, particularly preferably hydrochlorides.

In a preferred embodiment the dosage form according to the invention contains one active substance with abuse potential (A) or more active substance with abuse potentials (A) selected from the group consisting of 1,1-(3-dimethylamino-3-phenylpentamethylen)-6-fluor-1,3,4,9-tetrahydropyrano[3,4-b]indole, in particular its hemicitrate; 1,1-[3-dimethylamino-3-(2-thienyl)pentamethylen]-1,3,4,9-tetrahydropyrano[3,4-b]indole, in particular its citrate; and 1,1-[3-dimethylamino-3-(2-thienyl)pentamethylen]-1,3,4,9-tetrahydropyrano[3,4-b]-6-fluoro-indole, in particular its hemicitrate. These compounds are known, for example, from WO 2004/043967 or WO 2005/066183. The disclosure of these references is expressly incorporated herein and made a part of this present application.

The amount of the active substance with abuse potential (A), based on the total amount of the dosage form, is preferably within the range from 0.01 to 95 wt.-%, more preferably from 0.5 to 80 wt.-%, still more preferably 1.0 to 70 wt.-%, most preferably 5.0 to 60 wt.-% and in particular 10 to 50 wt.-%. In a preferred embodiment it is more than 20 wt.-%.

The dosage form according to the invention is in particular suitable for preventing abuse of an opioid active ingredient selected from the group comprising oxycodone, hydromorphone, morphine, tramadol and the physiologically acceptable derivatives or compounds thereof, preferably the salts and solvates thereof, preferably the hydrochlorides thereof.

The dosage form according to the invention is furthermore in particular suitable for preventing abuse of an opioid active ingredient selected from the group comprising (1R,2R)-3-(3-dimethylamino-1-ethyl-2-methyl-propyl)-phenol, (2R,3R)-1-dimethylamino-3-(3-methoxy-phenyl)-2-methyl-pentan-3-ol, (1RS,3RS,6RS)-6-dimethylaminomethyl-1-(3-methoxyphenyl)-cyclohexane-1,3-diol, (1R,2R)-3-(2-dimethylaminoethylcyclohexyl)-phenol, the physiologically acceptable salts thereof, preferably hydrochlorides, physiologically acceptable enantiomers, stereoisomers, diastereomers and racemates and the physiologically acceptable derivatives thereof, preferably ethers, esters or amides.

These compounds and processes for the production thereof are described in EP-A-693475 or EP-A-780369. The disclosure of these references is expressly incorporated herein and made a part of this present application.

In order to achieve the necessary breaking strength of the dosage form according to the invention, at least one synthetic or natural polymer (C) is used. The polymer (C) contributes to the breaking strength of the dosage form of at least 500 N, measured using the method disclosed in the specification. At least one polymer selected from the group comprising polyalkylene oxides, preferably polymethylene oxide, polyethylene oxide, polypropylene oxide; polyethylene, polypropylene, polyvinyl chloride, polycarbonate, polystyrene, polyacrylate, copolymers thereof, and mixtures of at least two of the stated polymers is preferably used for this purpose. High molecular weight thermoplastic polyalkylene oxides are preferred. High molecular weight polyethylene oxides with a molecular weight of at least 0.5 million, preferably of at least 1 million up to 15 million, determined by rheological measurements, are particularly preferred. These polymers have a viscosity at 25° C. of 4500 to 17600 cP, measured on a 5 wt. % aqueous solution using a model RVF Brookfield viscosimeter (spindle no. 2/rotational speed 2 rpm), of 400 to 4000 cP, measured on a 2 wt. % aqueous solution using the stated viscosimeter (spindle no. 1 or 3/rotational speed 10 rpm) or of 1650 to 10000 cP, measured on a 1 wt. % aqueous solution using the stated viscosimeter (spindle no. 2/rotational speed 2 rpm).

The polymers are preferably used in powder form. They may be soluble in water.

In order to achieve the necessary breaking strength of the dosage form according to the invention, it is furthermore possible additionally to use at least one natural or synthetic wax (D). The wax (D) contributes to the breaking strength of the dosage form of at least 500 N, measured using the method disclosed in the specification. Waxes with a softening point of at least 60° C. are preferred. Carnauba wax and beeswax are particularly preferred. Carnauba wax is very particularly preferred. Carnauba wax is a natural wax which is obtained from the leaves of the carnauba palm and has a softening point of at least 80° C. When the wax component is additionally used, it is used together with at least one polymer (C) in quantities such that the dosage form has a breaking strength of at least 500 N.

In a preferred embodiment, the breaking strength of the dosage form amounts to at least 500 N, to at least 600 N, to at least 700 N, to at least 800 N, to at least 900 N, to at least 1000 N or even to at least 1100 N.

Component (C) is preferably used in an amount of 20 to 99.9 wt. %, particularly preferably of at least 30 wt. %, very particularly preferably of at least 40 wt. %, relative to the total weight of the dosage form.

In increasingly preferred embodiments, the dosage form according to the invention has a density of at least 0.80 or at least 0.85 g/cm$^3$, at least 0.90 or at least 0.95 g/cm$^3$, at least 1.00, at least 1.05 or at least 1.10 g/cm$^3$, in the range from 0.80 to 1.35 g/cm$^3$, and in particular in the range from 0.95 to 1.25 g/cm$^3$.

The dosage form according to the invention is characterized by a comparatively homogeneous distribution of density. Preferably, the densities of two segments of the dosage form having a volume of 1.0 mm$^3$ each, deviate from one another by not more than ±10%, or by not more than ±7.5%, or by not more than ±5.0%, most preferably not more than ±2.5%, and in particular not more than ±1.0%.

The dosage form according to the invention is characterized by a comparatively homogeneous distribution of the active substance with abuse potential (A). Preferably, the content of component (A) in two segments of the dosage form having a volume of 1.0 mm$^3$ each, deviates from one another by not more than ±10%, more preferably not more than more than ±7.5%, still more preferably not more than ±5.0%, most preferably not more than ±2.5%, and in particular not more than ±1.0%.

Preferably, the total weight of the dosage form according to the invention is within the range from 0.01 g to 1.5 g, more preferably 0.05 g to 1.2 g, still more preferably 0.1 g to 1.0 g, most preferably 0.2 g to 0.9 g and in particular 0.25 g to 0.8 g.

Auxiliary substances (B) which may be used are those known auxiliary substances which are conventional for the formulation of solid dosage forms. These are preferably plasticizers, such as polyethylene glycol, auxiliary substances which influence active ingredient release, preferably hydrophobic or hydrophilic, preferably hydrophilic polymers, very particularly preferably hydroxypropylcellulose, and/or antioxidants. Suitable antioxidants are ascorbic acid, butylhydroxyanisole, butylhydroxytoluene, salts of ascorbic acid, monothioglycerol, phosphorous acid, vitamin C, vitamin E and the derivatives thereof, sodium bisulfite, particularly preferably butylhydroxytoluene (BHT) or butylhydroxyanisole (BHA) and α-tocopherol.

The antioxidant is preferably used in quantities of 0.01 to 10 wt. %, preferably of 0.03 to 5 wt. %, relative to the total weight of the dosage form.

The dosage forms according to the invention are distinguished in that, due their hardness, they cannot be pulverized in conventional comminution means available to an abuser, such as a mortar and pestle. This virtually rules out oral or parenteral, in particular intravenous or nasal abuse. However, in order to prevent any possible abuse of the dosage form according to the invention, the dosage forms according to the invention may, in a preferred embodiment, contain further agents which complicate or prevent abuse as auxiliary substances (B).

The abuse-proofed dosage form according to the invention, which comprises, apart from one or more active ingredients with abuse potential, at least one hardening polymer (C) and optionally at least one wax (D), may accordingly also comprise at least one of the following components (a)-(e) as auxiliary substances (B):

at least one substance which irritates the nasal passages and/or pharynx, at least one viscosity-increasing agent, which, with the assistance of a necessary minimum quantity of an aqueous liquid, forms a gel with the extract obtained from the dosage form, which gel preferably remains visually distinguishable when introduced into a further quantity of an aqueous liquid, at least one antagonist for each of the active ingredients with abuse potential, at least one emetic, at least one dye as an aversive agent, at least one bitter substance.

Components (a) to (f) are additionally each individually suitable for abuse-proofing the dosage form according to the invention. Accordingly, component (a) is preferably suitable for proofing the dosage form against nasal, oral and/or parenteral, preferably intravenous, abuse, component (b) is preferably suitable for proofing against parenteral, particularly preferably intravenous and/or nasal abuse, component (c) is preferably suitable for proofing against nasal and/or parenteral, particularly preferably intravenous, abuse, component (d) is preferably suitable for proofing against parenteral, particularly preferably intravenous, and/or oral and/or nasal abuse, component (e) is suitable as a visual deterrent against oral or parenteral abuse and component (f) is suitable for proofing against oral or nasal abuse. Combined use according to the invention of at least one of the above-stated components makes it possible still more effectively to prevent abuse of dosage forms according to the invention.

In one embodiment, the dosage form according to the invention may also comprise two or more of components (a)-(f) in a combination, preferably (a), (b) and optionally (c) and/or (f) and/or (e) or (a), (b) and optionally (d) and/or (f) and/or (e).

In another embodiment, the dosage form according to the invention may comprise all of components (a)-(f).

If the dosage form according to the invention comprises component (a) to counter abuse, substances which irritate the nasal passages and/or pharynx which may be considered according to the invention are any substances which, when administered via the nasal passages and/or pharynx, bring about a physical reaction which is either so unpleasant for the abuser that he/she does not wish to or cannot continue administration, for example burning, or physiologically counteracts taking of the corresponding active ingredient, for example due to increased nasal secretion or sneezing. These substances which conventionally irritate the nasal passages and/or pharynx may also bring about a very unpleasant sensation or even unbearable pain when administered parenterally, in particular intravenously, such that the abuser does not wish to or cannot continue taking the substance.

Particularly suitable substances which irritate the nasal passages and/or pharynx are those which cause burning, itching, an urge to sneeze, increased formation of secretions or a combination of at least two of these stimuli. Appropriate substances and the quantities thereof which are conventionally to be used are known per se to the person skilled or may be identified by simple preliminary testing.

The substance which irritates the nasal passages and/or pharynx of component (a) is preferably based on one or more constituents or one or more plant parts of at least one hot substance drug.

Corresponding hot substance drugs are known per se to the person skilled in the art and are described, for example, in "Pharmazeutische Biologie—Drogen und ihre Inhaltsstoffe" by Prof. Dr. Hildebert Wagner, 2nd., revised edition, Gustav Fischer Verlag, Stuttgart-New York, 1982, pages 82 et seq. The disclosure of these references is expressly incorporated herein and made a part of this present application.

A dosage unit is taken to mean a separate or separable administration unit, such as for example a tablet or a capsule.

One or more constituents of at least one hot substance drug selected from the group consisting of *Allii sativi bulbus* (garlic), *Asari rhizoma cum herba* (Asarum root and leaves), *Calami rhizoma* (calamus root), *Capsici fructus* (capsicum), *Capsici fructus acer* (cayenne pepper), *Curcumae longae rhizoma* (turmeric root), *Curcumae xanthorrhizae rhizoma* (Javanese turmeric root), *Galangae rhizoma* (galangal root), *Myristicae semen* (nutmeg), *Piperis nigri fructus* (pepper), *Sinapis albae semen* (white mustard seed), *Sinapis nigri semen* (black mustard seed), *Zedoariae rhizoma* (zedoary root) and *zingiberis rhizoma* (ginger root), particularly preferably from the group consisting of *Capsici fructus* (capsicum), *Capsici fructus acer* (cayenne pepper) and *Piperis nigri fructus* (pepper) may preferably be added as component (a) to the dosage form according to the invention.

The constituents of the hot substance drugs preferably comprise o-methoxy(methyl)phenol compounds, acid amide compounds, mustard oils or sulfide compounds or compounds derived therefrom.

Particularly preferably, at least one constituent of the hot substance drugs is selected from the group consisting of myristicin, elemicin, isoeugenol, α-asarone, safrole, gingerols, xanthorrhizol, capsaicinoids, preferably capsaicin, capsaicin derivatives, such as N-vanillyl-9E-octadecenamide, dihydrocapsaicin, nordihydrocapsaicin, homocapsaicin, norcapsaicin and nomorcapsaicin, piperine, preferably transpiperine, glucosinolates, preferably based on non-volatile mustard oils, particularly preferably based on p-hydroxybenzyl mustard oil, methylmercapto mustard oil or methylsulfonyl mustard oil, and compounds derived from these constituents.

The dosage form according to the invention may preferably contain the plant parts of the corresponding hot substance drugs in a quantity of 0.01 to 30 wt. %, particularly preferably of 0.1 to 0.5 wt. %, in each case relative to the total weight of the dosage unit.

If one or more constituents of corresponding hot substance drugs are used, the quantity thereof in a dosage unit according to the invention preferably amounts to 0.001 to 0.005 wt. %, relative to the total weight of the dosage unit.

Another option for preventing abuse of the dosage form according to the invention consists in adding at least one viscosity-increasing agent as a further abuse-preventing component (b) to the dosage form, which, with the assistance of a necessary minimum quantity of an aqueous liquid, forms a gel with the extract obtained from the dosage form, which gel is virtually impossible to administer safely and preferably remains visually distinguishable when introduced into a further quantity of an aqueous liquid.

For the purposes of the present invention, visually distinguishable means that the active ingredient-containing gel formed with the assistance of a necessary minimum quantity of aqueous liquid, when introduced, preferably with the assistance of a hypodermic needle, into a further quantity of aqueous liquid at 37° C., remains substantially insoluble and cohesive and cannot straightforwardly be dispersed in such a manner that it can safely be administered parenterally, in particular intravenously. The material preferably remains visually distinguishable for at least one minute, preferably for at least 10 minutes.

The increased viscosity of the extract makes it more difficult or even impossible for it to be passed through a needle or injected. If the gel remains visually distinguishable, this means that the gel obtained on introduction into a further quantity of aqueous liquid, for example by injection into blood, initially remains in the form of a largely cohesive thread, which, while it may indeed be broken up into smaller fragments, cannot be dispersed or even dissolved in such a manner that it can safely be administered parenterally, in particular intravenously. In combination with at least one optionally present component (a) to (e), this additionally leads to unpleasant burning, vomiting, bad flavor and/or visual deterrence.

Intravenous administration of such a gel would most probably result in obstruction of blood vessels, associated with serious harm to the health of the abuser.

In order to verify whether a viscosity-increasing agent is suitable as component (b) for use in the dosage form according to the invention, the active ingredient is mixed with the viscosity-increasing agent and suspended in 10 ml of water at a temperature of 25° C. If this results in the formation of a gel which fulfils the above-stated conditions, the corresponding viscosity-increasing agent is suitable for preventing or averting abuse of the dosage forms according to the invention.

If component (b) is added to the dosage form according to the invention, one or more viscosity-increasing agents are used which are selected from the group comprising microcrystalline cellulose containing carboxymethylcellulose sodium (e.g. Avicel® RC 591, FMC Corporation, Philadelphia, Pa., US), carboxymethylcellulose sodium (Blanose® Hercules Inc., Wilmington, US; CMC-Na C300P®, Cesalpinia Food S.p.A., Milano, IT; Frimulsion BLC-5®, Cesalpinia Food S.p.A., Milano, IT; Tylose C300 P® SE Tylose GmbH & Co. KG, Wiesbaden, DE), polyacrylic acid (Carbopol® 980 NF, Noveon IP Holdings Corp., Cleveland, Ohio, US, Carbopol® 981, Noveon IP Holdings Corp., Cleveland, Ohio, US), locust bean flour (Cesagum® LA-200, Cesalpinia Food S.p.A., Milano, IT; Cesagum® LID/150, Cesalpinia Food S.p.A., Milano, IT; Cesagum® LN-1, Cesalpinia Food S.p.A., Milano, IT), pectins, preferably from citrus fruits or apples (Cesapectin® HM Medium Rapid Set, Cesalpinia Food S.p.A., Milano, IT), waxy maize starch (C*Gel 04201®, Cerestar Deutschland GmbH, Krefeld, DE), sodium alginate (Frimulsion ALG (E401)®, Cesalpinia Food S.p.A., Milano, IT), guar flour (Frimulsion BM®, Cesalpinia Food S.p.A., Milano, IT; Polygum 26/1-75®, Polygal AG, Marstetten, CH), iota carrageen (Frimulsion D021®, Cesalpinia Food S.p.A., Milano, IT), karaya gum, gellan gum (Kelcogel F®, Kelcogel LT100®, CP Kelco ApS, Lille Skensved, DK), galactomannan (Meyprogat 150®, Meyhall Chemical, Kreuzlingen, CH), tara bean flour (Polygum 43/1®, Polygal AG, Marstetten, CH), propylene glycol alginate (Protanal-Ester SD-LB®, FCM Biopolymer AS, Drammen, NO), sodium hyaluronate, tragacanth, tara gum (Vidogum SP 200® Unipektin AG, Zurich, CH), fermented polysaccharide welan gum (K1A96), xanthan gum (Xantural 180®). Xanthans are particularly preferred. The names stated in brackets are the trade names by which the materials are known commercially. In general, a quantity of 0.1 to 20 wt. %, particularly preferably of 0.1 to 15 wt. % of the stated viscosity-increasing agent(s) is sufficient to fulfill the above-stated conditions The component (b) viscosity-increasing agents, where provided, are preferably present in the dosage form according to the invention in quantities of ≧5 mg per dosage unit, i.e. per administration unit.

In a particularly preferred embodiment of the present invention, the viscosity-increasing agents used as component (b) are those which, on extraction from the dosage form with the necessary minimum quantity of aqueous liquid, form a gel which encloses air bubbles. The resultant gels are distinguished by a turbid appearance, which provides the potential abuser with an additional optical warning and discourages him/her from administering the gel parenterally.

Component (C) may also optionally serves as an additional viscosity-increasing agent which, with the assistance of a minimum necessary quantity of an aqueous liquid, forms a gel.

It is also possible to formulate the viscosity-increasing agent and the other constituents in the dosage form according to the invention in a mutually spatially separated arrangement.

In order to discourage and prevent abuse, the dosage form according to the invention may furthermore comprise component (c), namely one or more antagonists for the active ingredient or active ingredients with abuse potential, wherein the antagonists are preferably spatially separated from the remaining constituents of the invention dosage according to the form and, when correctly used, do not exert any effect.

Suitable antagonists for preventing abuse of the active ingredients are known per se to the person skilled in the art and may be present in the dosage form according to the invention as such or in the form of corresponding derivatives, in particular esters or ethers, or in each case in the form of corresponding physiologically acceptable compounds, in particular in the form of the salts or solvates thereof.

If the active ingredient present in the dosage form is an opioid, the antagonist used is preferably an antagonist selected from the group comprising naloxone, naltrexone, nalmefene, nalid, nalmexone, nalorphine or naluphine, in each case optionally in the form of a corresponding physiologically acceptable compound, in particular in the form of a base, a salt or solvate. The corresponding antagonists, where component (c) is provided, are preferably used in a quantity of ≧1 mg, particularly preferably in a quantity of 3 to 100 mg, very particularly preferably in a quantity of 5 to 50 mg per dosage form, i.e. per administration unit.

If the dosage form according to the invention comprises a stimulant as active ingredient, the antagonist is preferably a neuroleptic, preferably at least one compound selected from the group consisting of haloperidol, promethazine, fluphenazine, perphenazine, levomepromazine, thioridazine, perazine, chlorpromazine, chlorprothixine, zuclopentixol, flupentixol, prothipendyl, zotepine, benperidol, pipamperone, melperone and bromperidol.

The dosage form according to the invention preferably comprises these antagonists in a conventional therapeutic dose known to the person skilled in the art, particularly preferably in a quantity of twice to four times the conventional dose per administration unit.

If the combination to discourage and prevent abuse of the dosage form according to the invention comprises component (d), it may comprise at least one emetic, which is preferably present in a spatially separated arrangement from the other components of the dosage form according to the invention and, when correctly used, is intended not to exert its effect in the body.

Suitable emetics for preventing abuse of an active ingredient are known per se to the person skilled in the art and may be present in the dosage form according to the invention as such or in the form of corresponding derivatives, in particular esters or ethers, or in each case in the form of corresponding physiologically acceptable compounds, in particular in the form of the salts or solvates thereof.

An emetic based on one or more constituents of ipecacuanha (ipecac) root, preferably based on the constituent emetine may preferably be considered in the dosage form according to the invention, as are, for example, described in "Pharmazeutische Biologie—Drogen und ihre Inhaltsstoffe" by Prof. Dr. Hildebert Wagner, 2nd, revised edition, Gustav Fischer Verlag, Stuttgart, New York, 1982. The disclosure of these references is expressly incorporated herein and made a part of this present application.

The dosage form according to the invention may preferably comprise the emetic emetine as component (d), preferably in a quantity of ≧3 mg, particularly preferably of ≧10 mg and very particularly preferably in a quantity of ≧20 mg per dosage form, i.e. administration unit.

Apomorphine may likewise preferably be used as an emetic in the abuse-proofing according to the invention, preferably in a quantity of preferably ≧3 mg, particularly preferably of ≧5 mg and very particularly preferably of ≧7 mg per administration unit.

If the dosage form according to the invention contains component (e) as a further abuse-preventing auxiliary substance, the use of a such a dye brings about an intense coloration of a corresponding aqueous solution, in particular when the attempt is made to extract the active ingredient for parenteral, preferably intravenous administration, which coloration may act as a deterrent to the potential abuser. Oral abuse, which conventionally begins by means of aqueous extraction of the active ingredient, may also be prevented by this coloration. Suitable dyes and the quantities required for the necessary deterrence may be found in WO 03/015531. The disclosure of this reference is expressly incorporated herein and made a part of this present application.

If the dosage form according to the invention contains component (f) as a further abuse-preventing auxiliary substance, this addition of at least one bitter substance and the consequent impairment of the flavor of the dosage form additionally prevents oral and/or nasal abuse.

Suitable bitter substances and the quantities effective for use may be found in US-2003/0064099 A1. The disclosure of this reference is expressly incorporated herein and made a part of this present application. Suitable bitter substances are preferably aromatic oils, preferably peppermint oil, eucalyptus oil, bitter almond oil, menthol, fruit aroma substances, preferably aroma substances from lemons, oranges, limes, grapefruit or mixtures thereof, and/or denatonium benzoate (Bitrex®). Denatonium benzoate is particularly preferred.

The solid dosage form according to the invention is suitable to be taken orally, vaginally or rectally, preferably orally. The dosage form is preferably not in film form.

The dosage form according to the invention may assume multiparticulate form, preferably in the form of microtablets, microcapsules, micropellets, granules, spheroids, beads or pellets, optionally packaged in capsules or pressed into tablets, preferably for oral administration. The multiparticulate forms preferably have a size or size distribution in the range from 0.1 to 3 mm, particularly preferably in the range from 0.5 to 2 mm. Depending on the desired dosage form, conventional auxiliary substances (B) are optionally also used for the formulation of the dosage form.

The solid, abuse-proofed dosage form according to the invention is preferably produced by thermoforming with the assistance of an extruder without any observable consequent discoloration of the extrudates.

In order to investigate the extent of discoloration due to this thermoforming, the color of the mixture of starting components of which the dosage form consists is first determined without addition of a color-imparting component, such as for example a coloring pigment or an intrinsically colored component (for example α-tocopherol). This composition is then thermoformed according to the invention, wherein all process steps, including cooling of the extrudate, are preferably performed under an inert gas atmosphere. By way of comparison, the same composition is produced by the same process, but without an inert gas atmosphere. The color of the dosage form produced according to the invention from the starting composition and of the dosage form produced by way of comparison is determined. The determination is performed with the assistance of "Munsell Book of Color" from Munsell Color Company Baltimore, Md., USA, 1966 edition. If the color of the dosage form thermoformed according to the invention has a color with identification no. N 9.5, but at most a color with the identification no. 5Y 9/1, thermoforming is classed as being "without discoloration". If the dosage form has a color with the identification no. 5Y 9/2 or greater, as determined according to the Munsell Book of Color, the thermoforming is classed as being "with discoloration".

Surprisingly, the dosage forms according to the invention exhibit no discoloration classed in accordance with the above classification, if the entire production process is performed under an inert gas atmosphere, preferably under a nitrogen atmosphere with the assistance of an extruder for thermoforming.

In one embodiment of the present invention the abuse-proofed dosage forms are produced by a process comprising mixing components (A), the optionally present component (B), (C) and the optionally present component (D) and co-mixing the optionally present components a) to f) or, if necessary, separately mixing with the addition of component (C) and optionally (D), heating the resultant mixture or the resultant mixtures in the extruder at least up to the softening point of component (C) and extruding the mixture through the outlet orifice of the extruder by application of force, singulating and forming the still plastic extrudate into the dosage form or cooling and forming the extrudate into the dosage form, wherein process steps II) and III) and optionally process steps I) and IV) are optionally performed under an inert gas atmosphere, preferably a nitrogen atmosphere.

Mixing of the components according to process step I) may also proceed in the extruder.

Mixing of components (A), optionally (B), (C) and optionally (D) and of the optionally present further components (a)-(f) and optionally components (C) and the optionally present component (D) may also optionally proceed in a mixer known to the person skilled in the art. The mixer may, for example, be a roll mixer, shaking mixer, shear mixer or compulsory mixer.

Before blending with the remaining components, component (C) and the optionally present component (D) is preferably provided according to the invention with an antioxidant. This may proceed by mixing the two components, (C) and the antioxidant, preferably by dissolving or suspending the antioxidant in a highly volatile solvent and homogeneously mixing this solution or suspension with component (C) and the optionally present component (D) and removing the solvent by drying, preferably under an inert gas atmosphere. Alternatively, a physiologically acceptable auxiliary substance (B) or a wax (D) may serve as the solvent, preferably at elevated temperature. For example, when polyethylene glycol is used as a plasticizer, it may be molten or liquefied at moderately elevated temperature and the antioxidant may be dissolved therein. Under these circumstances the highly volatile solvent can be omitted.

The dosage forms according to the invention which contain subunits with further auxiliary substances which prevent or complicate abuse may be produced by coextruding or separately extruding the mixtures according to step I).

In any event, the, preferably molten, mixture or mixtures which has/have been heated in the extruder at least up to the softening point of component (C) is/are extruded from the extruder through a die with at least one bore.

The process according to the invention is preferably performed using conventional screw extruders, particularly preferably twin-screw-extruders.

The extruder preferably comprises at least two temperature zones, with heating of the mixture at least up to the softening point of component (C) proceeding in the first zone, which is downstream from a feed zone and optionally mixing zone. The throughput of the mixture is preferably from 2.0 kg to 8.0 kg/hour.

After heating at least up to the softening point of component (C), the molten mixture is conveyed with the assistance of the screws, further homogenized, compressed or compacted such that, immediately before emerging from the extruder die, it exhibits a minimum pressure of 5 bar, preferably of at least 10 bar, and is extruded through the die as an extruded strand or strands, depending on the number of bores which the die comprises. The die geometry or the geometry of the bores is freely selectable. The die or the bores may accordingly exhibit a round, oblong or oval cross-section, wherein the round cross-section preferably has a diameter of 0.1 mm to 15 mm and the oblong cross-section preferably has a maximum lengthwise extension of 21 mm and a crosswise extension of 10 mm. Preferably, the die or the bores have a round cross-section. The casing of the extruder used according to the invention may be heated or cooled. The corresponding temperature control, i.e. heating or cooling, is so arranged that the mixture to be extruded exhibits at least an average temperature (product temperature) corresponding to the softening temperature of component (C) and does not rise above a temperature at which the active substance with abuse potential which is to be processed may be damaged. Preferably, the temperature of the mixture to be extruded is adjusted to below 180° C., preferably below 150° C., but at least to the softening temperature of component (C).

In general, the following parameters are critical in extrusion processes and have the consequences described:

1. Throughput (kg Per Hour)

If the throughput is too low the extruder is not correctly filled and the material is stressed thereby affecting the viscosity and the release profile of the final product; if the throughput is too high the load of the extruder is higher than 100% and the extruder shuts down automatically; and if the throughput is tolerable but close to the upper limit significant expansion of the extruded strand occurs (also known as "die swelling").

2. Screw Geometry

A minimum number of kneading elements is required in order to obtain a homogeneous mixture; if the number is too high, the material is stressed thereby affecting the viscosity and the release profile of the final product. The number and lead of the conveying elements influences the homogeneity of the mixture and its residence time in the extruder and controls the increase of the pressure in front of the die. Mixing elements improve the homogeneity of the mixture; and eccentric screw heads allow for a continuous discharge of the extrudate without density variations.

3. Die and Merge Element Geometry

The geometry of the element which merges the extrusion strands in front of the die, and geometry of the die itself, the residence time in said element, and the ratio length of the die to diameter of the die influence the compression of the material thereby affecting the melt pressure. The die pressure depends on revolution, throughput and melt temperature and affects the viscosity and the release profile of the final product.

4. Temperature (Melt Zones)

The feeding cylinder should not be heated to prevent the starting material from melting in the feeder and causing an accumulation. The number of cylinders is variable, the longer the extruder the longer the residence time. The temperature of the cylinders (except feeding cylinder) destroys the material if it is too high: if too low the material does not sufficiently melt thereby resulting in an inhomogeneous mixture and degradation. The die temperature, if separately set too low, causes the "extrusion skin" to not properly form thereby making further processing of the extrudate difficult.

5. Revolution of the Extruder

If the extruder revolution speed is too high the material is stressed thereby affecting the viscosity and the release profile of the final product. If the extruder revolution speed is too low the load of the extruder is higher than 100% and the extruder shuts down automatically; and inter alia the residence time depends on the revolution.

6. Arrangement of Cylinders

The position of feeding cylinder and length of the extruder are important. The degassing should be located close to the feeder in order to avoid air pockets in the product; and if one of the components is thermo-labile it may be separately fed into one of the rear cylinders.

7. Temperature of the Water Cooling

Cooling of the engine and control of the temperature of the extrusion cylinders are important parameters.

The process according to the invention requires the use of suitable extruders, preferably screw extruders. Screw extruders which are equipped with two screws (twin-screw-extruders) are particularly preferred. Single-screw extruders are preferably excluded.

The extrusion is preferably performed so that the expansion of the strand due to extrusion is not more than 50%, i.e. that when using a die with a bore having a diameter of e.g. 6 mm, the extruded strand should have a diameter of not more than 9 mm. More preferably, the expansion of the strand is not more than 40%, still more preferably not more than 35%, most preferably not more than 30% and in particular not more than 25%. It has been surprisingly found that if the extruded material in the extruder is exposed to a mechanical stress exceeding a certain limit, a significant expansion of the strand occurs thereby resulting in undesirable irregularities of the properties of the extruded strand, particularly its mechanical properties.

For example, extrusion may be performed by means of a twin-screw-extruder type Micro 27 GL 40 D (Leistritz, Nürnberg, Germany), screw diameter 18 mm. Screws having eccentric ends may be used. A heatable die with a round bore having a diameter of 8 mm may be used. The entire extrusion process may be performed under nitrogen atmosphere. The extrusion parameters may be adjusted e.g. to the following values: rotational speed of the screws: 100 Upm; delivery rate: 4 kg/h; product temperature: 125° C.; and jacket temperature: 120° C.

After extrusion of the molten mixture and optional cooling of the extruded strand or extruded strands, the extrudates are preferably singulated. This singulation may preferably be performed by cutting up the extrudates by means of revolving or rotating knives, water jet cutters, wires, blades or with the assistance of laser cutters.

An inert gas atmosphere is not necessary for intermediate or final storage of the optionally singulated extrudate or the final shape of the dosage form according to the invention.

The singulated extrudate may be pelletized with conventional methods or be press-molded into tablets in order to impart the final shape to the dosage form. It is, however, also possible not to singulate the extruded strands and, with the assistance of contrarotating calender rolls comprising opposing recesses in their outer sleeve, to form them into the final shape, preferably a tablet, and to singulate these by conventional methods.

Should the optionally singulated extrudate not immediately be formed into the final shape, but instead cooled for storage, after the period of storage an inert gas atmosphere, preferably a nitrogen atmosphere, may optionally be provided and may be maintained during heating of the stored extrudate up until plasticization and definitive shaping to yield the dosage form.

The application of force in the extruder onto the at least plasticized mixture is adjusted by controlling the rotational speed of the conveying device in the extruder and the geometry thereof and by dimensioning the outlet orifice in such a manner that the pressure necessary for extruding the plasticized mixture is built up in the extruder, preferably immediately prior to extrusion. The extrusion parameters which, for each particular composition, are necessary to give rise to a dosage form with a breaking strength of at least 500 N, may be established by simple preliminary testing.

The process according to the invention involves the extrusion of a composition comprising components (A), (C), optionally (B) and optionally (D). Preferably, extrusion is performed by means of twin-screw-extruders.

It has been surprisingly found that extrudates exhibiting an advantageous morphology are obtainable by means of twin-screw-extruders. It has been found that under suitable conditions the extrudate is surrounded by a shell which may be denoted as "extrusion skin". Said extrusion skin can be regarded as a collar-like or tubular structure forming a circumferential section of the extrudate about its longitudinal extrusion axis so that the outer surface of said collar-like or tubular structure forms the closed shell of the extrudate. Usually, only the front faces of the extrudate are not covered by said extrusion skin.

The extrusion skin surrounds the core of the extrudate in a collar-like or tubular arrangement and preferably is connected therewith in a seamless manner. The extrusion skin differs from said core in its morphology. Usually, the extrusion skin is visible with the naked eye in the cross-section of the extrudate, optionally by means of a microscope, since due to the different morphology of the material forming the extrusion skin and the material forming the core, the optical properties differ as well. It seems that during extrusion the material forming the extrusion skin is exposed to mechanical and thermal conditions differing from the conditions the core of the extrudate is exposed to. In consequence, a heterogeneous morphology of the extruded strand is obtained, which e.g. assumes radial symmetry when an extrusion die having circular shape is used. The material forming the extrusion skin and the material forming the core are usually distinguished by their morphology, preferably, however, not by their composition, particularly not by the relative content of components (A), (C), optionally (B) and optionally (D).

Usually the extrusion skin covers the entire shell of the extrudate like a one-piece collar, independently of what geometry has been chosen for the extrusion die. Therefore, the extrudate may assume circular, elliptic or other cross-sections.

The extrusion skin is preferably characterized by a unitary thickness. Preferably, the thickness of the extrusion skin is within the range from 0.1 to 4.0 mm, more preferably 0.15 to 3.5 mm, still more preferably 0.2 to 3.0 mm, most preferably 0.2 to 2.5 mm and in particular 0.2 to 2.0 mm. In a preferred embodiment the thickness of the extrusion skin in the sum over both opposing sides amounts to 0.5 to 50%, more preferably 1.0 to 40%, still more preferably 1.5 to 35%, most preferably 2.0 to 30% and in particular 2.5 to 25% of the diameter of the extrudate.

FIG. 1 shows a schematic view of extrudate (71) having a collar-like extrusion skin (72) entirely surrounding the core (73) about the longitudinal extrusion axis (74). The outer surface of extrusion skin (72) forms the shell (75) of the extrudate (71).

It has been surprisingly found that extrudates having an extrusion skin exhibit beneficial mechanical properties. They are particularly suitable as intermediates in the production of the dosage forms according to the invention, because they may be advantageously processed, in particular by singulating and/or forming.

When the dosage forms according to the invention are prepared by means of extrusion processes which lead to intermediates having an extrusion skin as described above, the dosage forms obtained therefrom are preferably also characterized by a particular morphology.

In a preferred embodiment those regions, which have formed the extrusion skin in the extruded intermediate, are still visible with the naked eye, optionally by means of a microscope, in the cross-section of the dosage form. This is because usually by further processing the extrudate, particularly by singulating and/or shaping, the different nature and thereby also the different optical properties of the material forming the extrusion skin and the material forming the core are maintained. In the following, that domain of the dosage forms which has emerged from the extrusion skin in the course of further processing the extruded intermediate, will be denoted as "tubular domain".

Preferably, the dosage form according to the invention comprises a tubular domain and a core located therein. Preferably, the tubular domain is connected with the core in a seamless manner. Preferably the tubular domain as well as the core have substantially the same chemical composition, i.e. substantially the same relative content of components (A), (C), optionally (B) and optionally (D). The material forming the tubular domain has a morphology differing from the material forming the core. Usually, this different morphology is also expressed in terms of different optical properties, so that the tubular domain and the core are visible with the naked eye in the cross-section of the dosage form.

In case that the dosage form has been coated, e.g. by a film coating, the tubular domain is located between the film coating and the core.

Since the dosage form according to the invention may be obtained in different ways from the extrudate containing the extrusion skin (intermediate), the tubular domain may take different arrangements and extensions within the dosage form according to the invention. All arrangements have in common, however, that the tubular domain partially covers the surface of the core, but usually not its entire surface. Preferably, two opposing surfaces of the core are not, or at least not fully covered by the tubular domain. In other words, preferably the tubular domain has two openings/blanks on opposing sides.

The thickness of the tubular domain may be uniform. It is also possible, however, that in the course of the processing, i.e. due to the subsequent shaping (e.g. press-forming) of the extrudate, various sections of the extrusion skin are expanded or compressed differently thereby leading to a variation of the thickness of the tubular domain within the dosage form.

Preferably the thickness of the tubular domain is within the range from 0.1 to 4.0 mm, more preferably 0.15 to 3.5 mm, still more preferably 0.2 to 3.0 mm, most preferably 0.2 to 2.5 mm and in particular 0.2 to 2.0 mm.

Figure 2A:
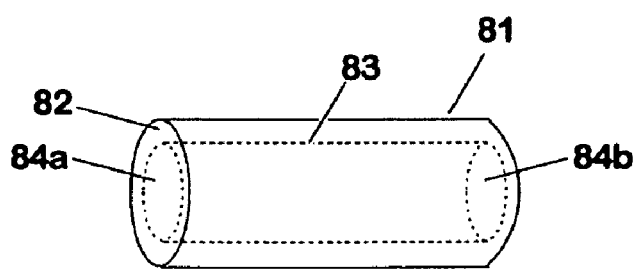
FIGS. 2A and 2B show schematic views of the preferred arrangements of the tubular domain within the dosage form.
Figure 2B:
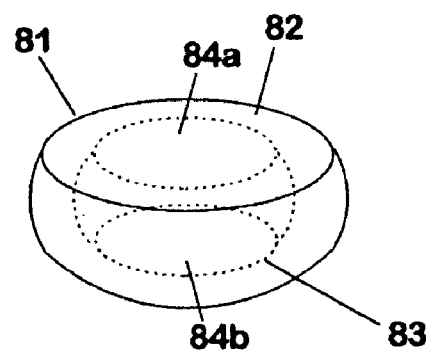

FIGS. 2A and 2B show schematic views of preferred arrangements of the tubular domain within the dosage form according to the invention. The dosage forms (81) contain a tubular domain (82) partially surrounding the core (83). The opposing surfaces (84*a*) and (84*b*) of the core (83), however, are not covered by the tubular domain (82).

The process for the preparation of the dosage form according to the invention is preferably performed continuously. Preferably, the process involves the extrusion of a homogeneous mixture of components (A), (C), optionally (B) and optionally (D). It is particularly advantageous if the obtained intermediate, e.g. the strand obtained by extrusion, exhibits uniform properties. Particularly desirable are uniform density, uniform distribution of the active substance, uniform mechanical properties, uniform porosity, uniform appearance of the surface, etc. Only under these circumstances the uniformity of the pharmacological properties, such as the stability of the release profile, may be ensured and the amount of rejects can be kept low.

Preferably, the process according to the present invention may be performed with less than 25% rejects, more preferably less than 20%, most preferably less than 15% and in particular less than 10% rejects, wherein the criteria for rejection are the FDA standards regarding the intervariability of the content of component (A), its release profile and/or the density of the dosage form when comparing two dosage forms, preferably taken from the same batch.

It has been surprisingly found that the above properties may be obtained by means of twin-screw-extruders.

The process according to the invention preferably involves the extrusion of a mixture of components (A), (C), optionally (B) and optionally (D), preferably by means of a twin-screw-extruder. After extrusion the extrudate is preferably singulated, shaped and optionally coated in order to obtain the final dosage form.

In a preferred embodiment of the process according to the invention, shaping is performed in the plasticized state of the mixture of components (A), (C), optionally (B) and optionally (D). It has been surprisingly found that the extrusion of certain polymers (C), particular of high molecular weight polyethylene oxides, yields intermediates exhibiting some kind of memory effect: when the singulated extrudates are shaped at ambient temperature, e.g. by press-forming, dosage forms are obtained which tend to regain their original outer form upon storage under stressed storage conditions, i.e. they return to the form they had prior to shaping.

The shape of the dosage form upon storage at stressed conditions, e.g. at 40° C./75% RH, may also be unstable for other reasons.

Said memory effect significantly deteriorates the storage stability of the dosage form, as by regaining its outer form several properties of the dosage form are changed. The same applies to any changes of the outer form due to other reasons.

It has been found that, for example, depending on the extrusion conditions a significant expansion of the strand may occur thereby resulting in an increase of the volume of the extrudate, i.e. a decrease of its density. Said expansion may be compensated by subsequently press-forming the singulated extrudate at a sufficient pressure, since under these conditions the expansion of the material may be reversed.

However, if press-forming has been performed at ambient temperature, the memory effect of the compressed extrudate will cause it to swell and to expand upon storage, thereby significantly increasing the volume of the dosage form.

It has been surprisingly found that such memory effect may be suppressed if shaping of the singulated extrudate is performed at increased temperature, i.e. in the plasticized state of the mixture of components (A), (C), optionally (B) and optionally (D). Preferably, shaping is performed at a pressure of at least 1 kN, more preferably within the range from 2 kN to 50 kN, e.g. by means of a tablet press. Preferably, shaping is performed at a temperature which preferably is about 40° C., more preferably about 30° C. and in particular about 25° C. below the melting range of the mixture of components (A), (C), optionally (B) and optionally (D). The melting range of a given mixture may be determined by conventional methods, preferably by DSC (e.g. with a DSC model 2920 (TA Instruments, New Castle) and ultrahigh pure nitrogen as purge gas at a flow rate of 150 ml/min; approximate sample weight of 10-20 mg, sealed in nonhermetic aluminium pans; temperature ramp speed 10° C./min).

In a preferred embodiment the outer shape of the dosage form according to the invention does not substantially change when being stored for at least 12 h, preferably for at least 24 h, at 40° C. and 75% RH, preferably in an open container.

In a preferred embodiment the volume of the dosage form according to the invention increases by not more than 20% or 17.5%, more preferably not more than 15% or 12.5%, still more preferably not more than 10% or 7.5%, most preferably not more than 6.0%, 5.0% or 4.0% and in particular not more than 3.0%, 2.0% or 1.0% when being stored for at least 12 h, preferably for at least 24 h, at a temperature of 20° C. below the melting range of the mixture of components (A), (C), optionally (B) and optionally (D), optionally at a temperature of 40° C. and 75% RH.

In a further preferred embodiment, the dosage form according to the invention assumes the form of a tablet, a capsule or is in the form of an oral osmotic therapeutic system (OROS), preferably if at least one further abuse-preventing component (a)-(f) is also present.

If components (c) and/or (d) and/or (f) are present in the dosage form according to the invention, care must be taken to ensure that they are formulated in such a manner or are present in such a low dose that, when correctly administered, the dosage form is able to bring about virtually no effect which impairs the patient or the efficacy of the active ingredient.

If the dosage form according to the invention contains component (d) and/or (f), the dosage must be selected such that, when correctly orally administered, no negative effect is caused. If, however, the intended dosage of the dosage form is exceeded in the event of abuse, nausea or an inclination to vomit or a bad flavor are produced. The particular quantity of component (d) and/or (f) which can still be tolerated by the patient in the event of correct oral administration may be determined by the person skilled in the art by simple preliminary testing.

If, however, irrespective of the fact that the dosage form according to the invention is virtually impossible to pulverize, the dosage form containing the components (c) and/or (d) and/or (f) is provided with protection, these components should preferably be used at a dosage which is sufficiently high that, when abusively administered, they bring about an intense negative effect on the abuser. This is preferably achieved by spatial separation of at least the active ingredient or active ingredients from components (c) and/or (d) and/or (f), wherein the active ingredient or active ingredients is/are present in at least one subunit (X) and components (c) and/or (d) and/or (f) is/are present in at least one subunit (Y), and wherein, when the dosage form is correctly administered, components (c), (d) and (f) do not exert their effect on taking and/or in the body and the remaining components of the formulation, in particular component (C) and optionally (D), are identical.

If the dosage form according to the invention comprises at least 2 of components (c) and (d) or (f), these may each be present in the same or different subunits (Y). Preferably, when present, all the components (c) and (d) and (f) are present in one and the same subunit (Y).

For the purposes of the present invention, subunits are solid formulations, which in each case, apart from conventional auxiliary substances known to the person skilled in the art, contain the active ingredient(s), at least one polymer (C) and the optionally present component (D) and optionally at least one of the optionally present components (a) and/or (b) and/or (e) or in each case at least one polymer (C) and optionally (D) and the antagonist(s) and/or emetic(s) and/or component (e) and/or component (f) and optionally at least one of the optionally present components (a) and/or (b). Care must here be taken to ensure that each of the subunits is formulated in accordance with the above-stated process.

One substantial advantage of the separated formulation of active ingredients from components (c) or (d) or (f) in subunits (X) and (Y) of the dosage form according to the invention is that, when correctly administered, components (c) and/or (d) and/or (f) are hardly released on taking and/or in the body or are released in such small quantities that they exert no effect which impairs the patient or therapeutic success or, on passing through the patient's body, they are only liberated in locations where they cannot be sufficiently absorbed to be effective. When the dosage form is correctly administered, preferably hardly any of components (c) and/or (d) and/or (f) is released into the patient's body or they go unnoticed by the patient.

The person skilled in the art will understand that the above-stated conditions may vary as a function of the particular components (c), (d) and/or (f) used and of the formulation of the subunits or the dosage form. The optimum formulation for the particular dosage form may be determined by simple preliminary testing. What is vital is that each subunit contains the polymer (C) and optionally component (D) and has been formulated in the above-stated manner.

Should, contrary to expectations, the abuser succeed in comminuting such a dosage form according to the invention, which comprises components (c) and/or (e) and/or (d) and/or (f) in subunits (Y), for the purpose of abusing the active ingredient and obtain a powder which is extracted with a suitable extracting agent, not only the active ingredient but also the particular component (c) and/or (e) and/or (f) and/or (d) will be obtained in a form in which it cannot readily be separated from the active ingredient, such that when the dosage form which has been tampered with is administered, in particular by oral and/or parenteral administration, it will exert its effect on taking and/or in the body combined with an additional negative effect on the abuser corresponding to component (c) and/or (d) and/or (f) or, when the attempt is made to extract the active ingredient, the coloration will act as a deterrent and so prevent abuse of the dosage form.

A dosage form according to the invention, in which the active ingredient or active ingredients is/are spatially separated from components (c), (d) and/or (e), preferably by formulation in different subunits, may be formulated in many different ways, wherein the corresponding subunits may each be present in the dosage form according to the invention in any desired spatial arrangement relative to one another, provided that the above-stated conditions for the release of components (c) and/or (d) are fulfilled.

The person skilled in the art will understand that component(s) (a) and/or (b) which are optionally also present may preferably be formulated in the dosage form according to the invention both in the particular subunits (X) and (Y) and in the form of independent subunits corresponding to subunits (X) and (Y), provided that neither the abuse-proofing nor the active ingredient release in the event of correct administration is impaired by the nature of the formulation and the polymer (C) and optionally (D) is included in the formulation and formulation is carried out in accordance with the above-stated process in order to achieve the necessary hardness.

In a preferred embodiment of the dosage form according to the invention, subunits (X) and (Y) are present in multiparticulate form, wherein microtablets, microcapsules, micropellets, granules, spheroids, beads or pellets are preferred and the same form, i.e. shape, is selected for both subunit (X) and subunit (Y), such that it is not possible to separate subunits (X) from (Y) by mechanical selection. The multiparticulate forms are preferably of a size in the range from 0.1 to 3 mm, preferably of 0.5 to 2 mm.

The subunits (X) and (Y) in multiparticulate form may also preferably be packaged in a capsule or be pressed into a tablet, wherein the final formulation in each case proceeds in such a manner that the subunits (X) and (Y) are also retained in the resultant dosage form.

The multiparticulate subunits (X) and (Y) of identical shape should also not be visually distinguishable from one another so that the abuser cannot separate them from one another by simple sorting. This may, for example, be achieved by the application of identical coatings which, apart from this disguising function, may also incorporate further functions, such as, for example, controlled release of one or more active ingredients or provision of a finish resistant to gastric juices on the particular subunits.

The multiparticulate subunits may also be formulated as an oral dosage form as a slurry or suspension in pharmaceutically safe suspending media.

In a further preferred embodiment of the present invention, subunits (X) and (Y) are in each case arranged in layers relative to one another.

The layered subunits (X) and (Y) are preferably arranged for this purpose vertically or horizontally relative to one another in the dosage form according to the invention, wherein in each case one or more layered subunits (X) and one or more layered subunits (Y) may be present in the dosage form, such that, apart from the preferred layer sequences (X)—(Y) or (X)—(Y)—(X), any desired other layer sequences may be considered, optionally in combination with layers containing components (a) and/or (b).

Another preferred dosage form according to the invention is one in which subunit (Y) forms a core which is completely enclosed by subunit (X), wherein a separation layer (Z) may be present between said layers. Such a structure is preferably also suitable for the above-stated multiparticulate forms, wherein both subunits (X) and (Y) and an optionally present separation layer (Z), which must satisfy the hardness requirement according to the invention, are formulated in one and the same multiparticulate form. In a further preferred embodiment of the dosage form according to the invention, the subunit (X) forms a core, which is enclosed by subunit (Y), wherein the latter comprises at least one channel which leads from the core to the surface of the dosage form.

The dosage form according to the invention may comprise, between one layer of the subunit (X) and one layer of the subunit (Y), in each case one or more, preferably one, optionally swellable separation layer (Z) which serves to separate subunit (X) spatially from (Y).

If the dosage form according to the invention comprises the layered subunits (X) and (Y) and an optionally present separation layer (z) in an at least partially vertical or horizontal arrangement, the dosage form preferably takes the form of a tablet, a coextrudate or a laminate.

In one particularly preferred embodiment, the entirety of the free surface of subunit (Y) and optionally at least part of the free surface of subunit(s) (X) and optionally at least part of the free surface of the optionally present separation layer(s) (Z) may be coated with at least one barrier layer (Z') which prevents release of component (c) and/or (e) and/or (d) and/or (f). The barrier layer (Z') must also fulfill the hardness conditions according to the invention.

Another particularly preferred embodiment of the dosage form according to the invention comprises a vertical or horizontal arrangement of the layers of subunits (X) and (Y) and at least one push layer (p) arranged therebetween, and optionally a separation layer (z), in which dosage form the entirety of the free surface of layer structure consisting of subunits (X) and (Y), the push layer and the optionally present separation layer (z) is provided with a semipermeable coating (E), which is permeable to a release medium, i.e. conventionally a physiological liquid, but substantially impermeable to the active ingredient and to component (c) and/or (d) and/or (f), and wherein this coating (E) comprises at least one opening for release of the active ingredient in the area of subunit (X).

A corresponding dosage form is known to the person skilled in the art, for example under the name oral osmotic therapeutic system (OROS), as are suitable materials and methods for the production thereof, inter alia from U.S. Pat. Nos. 4,612,008, 4,765,989 and 4,783,337. The disclosure of these references is expressly incorporated herein and made a part of this present application.

In a further preferred embodiment, the subunit (X) of the dosage form according to the invention is in the form of a tablet, the edge face of which and optionally one of the two main faces is covered with a barrier layer (Z') containing component (c) and/or (d) and/or (f).

The person skilled in the art will understand that the auxiliary substances of the subunit(s) (X) or (Y) and of the optionally present separation layer(s) (Z) and/or of the barrier layer(s) (Z') used in formulating the dosage form according to the invention will vary as a function of the arrangement thereof in the dosage form according to the invention, the mode of administration and as a function of the particular active ingredient of the optionally present components (a) and/or (b) and/or (e) and of component (c) and/or (d) and/or (f). The materials which have the requisite properties are in each case known per se to the person skilled in the art.

If release of component (c) and/or (d) and/or (f) from subunit (Y) of the dosage form according to the invention is prevented with the assistance of a cover, preferably a barrier layer, the subunit may consist of conventional materials known to the person skilled in the art, providing that it contains at least one polymer (C) and optionally (D) to fulfill the hardness condition of the dosage form according to the invention.

If a corresponding barrier layer (Z') is not provided to prevent release of component (c) and/or (d) and/or (f), the materials of the subunits should be selected such that release of the particular component (c) and/or (d) from subunit (Y) is virtually ruled out. The materials which are stated below to be suitable for production of the barrier layer may preferably be used for this purpose.

Preferred materials are those which are selected from the group comprising alkylcelluloses, hydroxyalkyl-celluloses, glucans, scleroglucans, mannans, xanthans, copolymers of poly[bis(p-carboxyphenoxy)propane and sebacic acid, preferably in a molar ratio of 20:80 (commercially available under the name Polifeprosan 20®), carboxymethylcelluloses, cellulose ethers, cellulose esters, nitrocelluloses, polymers based on (meth)acrylic acid and the esters thereof, polyamides, polycarbonates, polyalkylenes, polyalkylene glycols, polyalkylene oxides, polyalkylene terephthalates, polyvinyl alcohols, polyvinyl ethers, polyvinyl esters, halogenated polyvinyls, polyglycolides, polysiloxanes and polyurethanes and the copolymers thereof.

Particularly suitable materials may be selected from the group comprising methylcellulose, ethylcellulose, hydroxypropylcellulose, hydroxypropylmethylcellulose, hydroxybutylmethylcellulose, cellulose acetate, cellulose propionate (of low, medium or high molecular weight), cellulose acetate propionate, cellulose acetate butyrate, cellulose acetate phthalate, carboxymethylcellulose, cellulose triacetate, sodium cellulose sulfate, polymethyl methacrylate, polyethyl methacrylate, polybutyl methacrylate, polyisobutyl methacrylate, polyhexyl methacrylate, polyisodecyl methacrylate, polylauryl methacrylate, polyphenyl methacrylate, polymethyl acrylate, polyisopropyl acrylate, polyisobutyl acrylate, polyoctadecyl acrylate, polyethylene, low density polyethylene, high density polyethylene, polypropylene, polyethylene glycol, polyethylene oxide, polyethylene terephthalate, polyvinyl alcohol, polyvinyl isobutyl ether, polyvinyl acetate and polyvinyl chloride.

Particularly suitable copolymers may be selected from the group comprising copolymers of butyl methacrylate and isobutyl methacrylate, copolymers of methyl vinyl ether and maleic acid with high molecular weight, copolymers of methyl vinyl ether and maleic acid monoethyl ester, copolymers of methyl vinyl ether and maleic anhydride and copolymers of vinyl alcohol and vinyl acetate.

Further materials which are particularly suitable for formulating the barrier layer are starch-filled polycaprolactone (WO98/20073), aliphatic polyesteramides (DE 19 753 534 A1, DE 19 800 698 A1, EP 0 820 698 A1), aliphatic and aromatic polyester urethanes (DE 19822979), polyhydroxyalkanoates, in particular polyhydroxybutyrates, polyhydroxyvalerates, casein (DE 4 309 528), polylactides and copolylactides (EP 0 980 894 A1). The disclosure of these references is expressly incorporated herein and made a part of this present application.

The above-stated materials may optionally be blended with further conventional auxiliary substances known to the person skilled in the art, preferably selected from the group comprising glyceryl monostearate, semi-synthetic triglyceride derivatives, semi-synthetic glycerides, hydrogenated castor oil, glyceryl palmitostearate, glyceryl behenate, polyvinyl-pyrrolidone, gelatine, magnesium stearate, stearic acid, sodium stearate, talcum, sodium benzoate, boric acid and colloidal silica, fatty acids, substituted triglycerides, glycerides, polyoxyalkylene glycols and the derivatives thereof.

If the dosage form according to the invention comprises a separation layer (Z'), said layer, like the uncovered subunit (Y), may preferably consist of the above-stated materials described for the barrier layer. The person skilled in the art will understand that release of the active ingredient or of component (c) and/or (d) from the particular subunit may be controlled by the thickness of the separation layer.

The dosage form according to the invention exhibits controlled release of the active ingredient. It is preferably suitable for twice daily administration to patients.

The release properties of the dosage form according to the invention are substantially independent from the pH value of the release medium, i.e. preferably the release profile in artificial intestinal juice substantially corresponds to the release profile in artificial gastric juice. Preferably, at any given time point the release profiles deviate from one another by not more than 20%, more preferably not more than 15%, still more preferably not more than 10%, yet more preferably not more than 7.5%, most preferably not more than 5.0% and in particular not more than 2.5%.

Preferably, the dosage form according to the invention exhibits a uniform release profile. Preferably, the release profile of the active substance with abuse potential (A) is interindividually uniform (i.e. when comparing dosage forms obtained from the same process) and/or uniform within a single dosage form (i.e. when comparing segments of the same dosage form). Preferably, when comparing two probes each having a mass of preferably 500 mg, the total amount of the released active substance for any given time point of the measurement does not deviate by more than 20%, more preferably not more than 15%, still more preferably not more than 10%, yet more preferably not more than 7.5%, most preferably not more than 5.0% and in particular not more than 2.5%.

Preferably, the release profile of the dosage form according to the present invention is stable upon storage, preferably upon storage at elevated temperature, e.g. 37° C., for 3 month in sealed containers. In this regard "stable" means that when comparing the initial release profile with the release profile after storage, at any given time point the release profiles deviate from one another by not more than 20%, more preferably not more than 15%, still more preferably not more than 10%, yet more preferably not more than 7.5%, most preferably not more than 5.0% and in particular not more than 2.5%.

The dosage form according to the invention may comprise one or more active ingredients at least partially in controlled release form, wherein controlled release may be achieved with the assistance of conventional materials and methods known to the person skilled in the art, for example by embedding the active ingredient in a controlled release matrix or by the application of one or more controlled release coatings. Active ingredient release must, however, be controlled such that the above-stated conditions are fulfilled in each case, for example that, in the event of correct administration of the dosage form, the active ingredient or active ingredients are virtually completely released before the optionally present component (c) and/or (d) can exert an impairing effect. Addition of materials effecting controlled release must moreover not impair the necessary hardness.

Controlled release from the dosage form according to the invention is preferably achieved by embedding the active ingredient in a matrix. The auxiliary substances acting as matrix materials control active ingredient release. Matrix materials may, for example, be hydrophilic, gel-forming materials, from which active ingredient release proceeds mainly by diffusion, or hydrophobic materials, from which active ingredient release proceeds mainly by diffusion from the pores in the matrix.

Physiologically acceptable, hydrophobic materials which are known to the person skilled in the art may be used as matrix materials. Polymers, particularly preferably cellulose ethers, cellulose esters and/or acrylic resins are preferably used as hydrophilic matrix materials. Ethylcellulose, hydroxypropylmethylcellulose, hydroxypropylcellulose, hydroxymethylcellulose, poly(meth)acrylic acid and/or the derivatives thereof, such as the salts, amides or esters thereof are very particularly preferably used as matrix materials.

Matrix materials prepared from hydrophobic materials, such as hydrophobic polymers, waxes, fats, long-chain fatty acids, fatty alcohols or corresponding esters or ethers or mixtures thereof are also preferred. Mono- or diglycerides of C12-C30 fatty acids and/or C12-C30 fatty alcohols and/or waxes or mixtures thereof are particularly preferably used as hydrophobic materials.

It is also possible to use mixtures of the above-stated hydrophilic and hydrophobic materials as matrix materials.

Component (C) and the optionally present component (D), which serve to achieve the breaking strength of at least 500 N which is necessary according to the invention may furthermore also optionally serve as additional matrix materials.

If the dosage form according to the invention is intended for oral administration, it may also preferably comprise a coating which is resistant to gastric juices and dissolves as a function of the pH value of the release environment. By means of this coating, it is possible to ensure that the dosage form according to the invention passes through the stomach undissolved and the active ingredient is only released in the intestines. The coating which is resistant to gastric juices preferably dissolves at a pH value of between 5 and 7.5.

Corresponding materials and methods for the controlled release of active ingredients and for the application of coatings which are resistant to gastric juices are known to the person skilled in the art, for example from "Coated Pharmaceutical Dosage Forms—Fundamentals, Manufacturing Techniques, Biopharmaceutical Aspects, Test Methods and Raw Materials" by Kurt H. Bauer, K. Lehmann, Hermann P. Osterwald, Rothgang, Gerhart, 1st edition, 1998, Medpharm Scientific Publishers. The disclosure of these references is expressly incorporated herein and made a part of this present application.

Method for Determining the Breaking Strength

In order to verify whether a polymer may be used as component (C) or (D), the polymer is pressed to form a tablet with a diameter of 10 mm and a height of 5 mm using a force of 150 N at a temperature which at least corresponds to the softening point of the polymer and is determined with the assistance of a DSC diagram of the polymer. Using tablets produced in this manner, breaking strength is determined with the apparatus described below in accordance with the method for determining the breaking strength of tablets published in the European Pharmacopoeia 1997, page 143-144, method no. 2.9.8. The apparatus used for the measurement is a "Zwick Z 2.5" materials tester, Fmax=2.5 kN with a maximum draw of 1150 mm, which should be set up with 1 column and 1 spindle, a clearance behind of 100 mm and a test speed adjustable between 0.1 and 800 mm/min together with testControl software. Measurement is performed using a pressure piston with screw-in inserts and a cylinder (diam. 10 mm), a force transducer, Fmax. 1 kN, diameter=8 mm, class 0.5 from 10 N, class 1 from 2 N to ISO 7500-1, with manufacturer's test certificate M to DIN 55350-18 (Zwick gross force Fmax=1.45 kN) (all apparatus from Zwick GmbH & Co. KG, Ulm, Germany) with order no. BTC-FR 2.5 TH. D09 for the tester, order no. BTC-LC 0050N. P01 for the force transducer, order no. BO 70000 S06 for the centering device.

Figure 3:
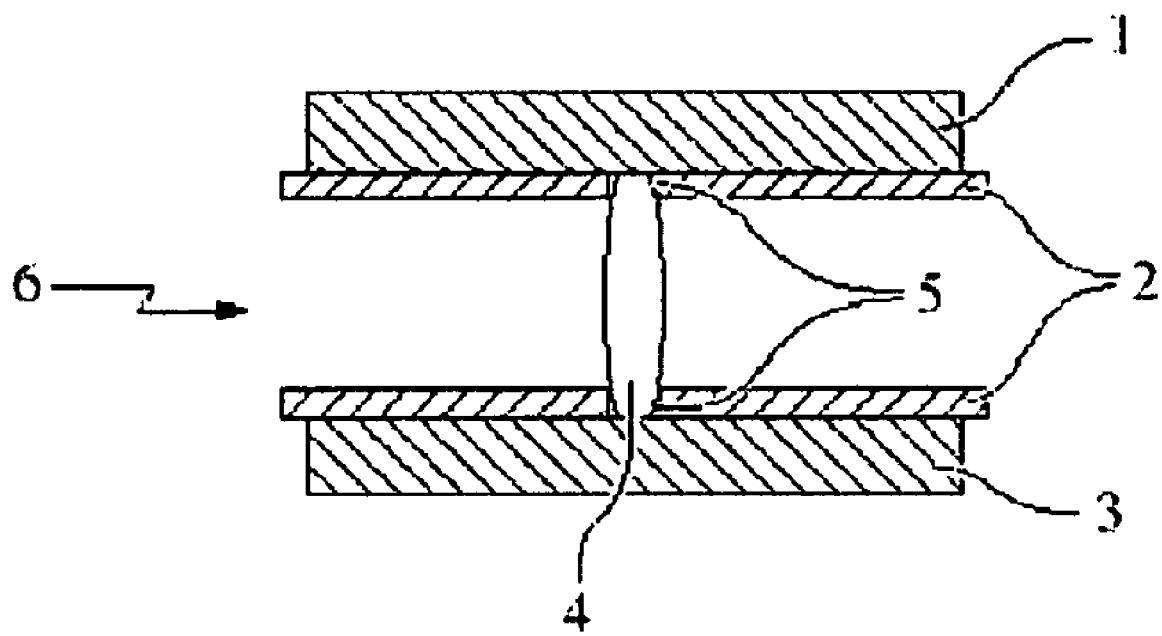
FIG. 3 shows the measurement of the breaking strength of a tablet.

FIG. 3 shows the measurement of the breaking strength of a tablet, in particular the tablet (4) adjustment device (6) used for this purpose before and during the measurement. To this end, the tablet (4) is held between the upper pressure plate (1) and the lower pressure plate (3) of the force application apparatus (not shown) with the assistance of two 2-part clamping devices, which are in each case firmly fastened (not shown) with the upper and lower pressure plate once the spacing (5) necessary for accommodating and centering the tablet to be measured has been established. The spacing (5) may be established by moving the 2-part clamping devices horizontally outwards or inwards in each case on the pressure plate on which they are mounted.

The tablets deemed to be resistant to breaking under a specific load include not only those which have not broken but also those which may have suffered plastic deformation under the action of the force.

In the case of the dosage forms according to the invention, breaking strength is determined in accordance with the stated method, dosage forms other than tablets also being tested.

The following Examples illustrate the invention purely by way of example and without restricting the general concept of the invention.

EXAMPLE 1

| Components | Per tablet | Per batch | |
|---|---|---|---|
| Tramadol HCl | 100.0 mg | 1495.0 g | |
| Polyethylene oxide, NF, MW 7 000 000 (Polyox WSR 303, Dow Chemicals) | 167.8 mg | 2508.6 g | |
| Hydroxypropylmethylcellulose 100 000 mPa · s | 33.5 mg | 500.8 g | |
| Polyethylene glycol (PEG 6000) | 33.5 mg | 500.8 g | |
| Butylhydroxytoluene (BHT) | 0.2 mg | 3.0 g | |
| Total weight | 335.0 mg | 5008.2 g | |

The stated quantity of BHT was dissolved in ethanol (96%), such that a 7.7% (mass/mass) ethanolic solution was obtained. This was mixed initially with 150 g of polyethylene oxide in a high speed mixer for 30 minutes and then the remaining quantity of polyethylene oxide was added and stirring continued for a further 30 minutes. The composition was dried for 12 h at 40° C. All the further components were added and mixed for 15 min in a free-fall mixer. The powder mixture was apportioned into an extruder. Extrusion was performed using a model Micro 27 GL 40 D double screw extruder with a spindle diameter of 18 mm manufactured by Leistritz (Nürnberg). Screws with blunt ends were used, the hex socket at the end of the screws being closed with a cap. The die used is a heatable round die with a diameter of 8 mm. The entire process was performed under an $N_2$ atmosphere.

The following parameters were selected for extrusion:

| | |
|---|---|
| Screw speed: | 100 rpm |
| Throughput: | 4 kg/h |
| Product temperature: | 125° C. |
| Casing temperature: | 120° C. |

The extrudate, which was still hot, was cooled under a nitrogen atmosphere. The cooled strand was singulated into biplanar tablets. The tablets did not break when exposed to a force of 500 N. The tablets could not be comminuted either with a hammer or with the assistance of a mortar and pestle.

The color of the cooled strand or of the 10 tablets singulated therefrom was determined at N 9.5/using the Munsell Book of Color, such that the dosage form produced by the process according to the invention did not exhibit any discoloration due to the thermoforming with the assistance of an extruder.

EXAMPLE 2

| Components | Per Tablet | Per batch | |
|---|---|---|---|
| Oxycodon HCl | 20.0 mg | 410.1 g | 13.7% |
| Polyethylene oxide 7 000 000 (Polyox WSR 303, DOW Chemicals) | 107.2 mg | 2199.3 g | 73.2% |
| Polyethylene glycol (PEG 6000) | 15.0 mg | 307.8 g | 10.3% |
| Hypromellose (Metholose 90 SH 100 000 cP, ShinEtsu) | 3.8 mg | 76.8 g | 2.6% |
| α-Tocopherol | 0.2 mg | 3.0 g | 0.1% |
| Aerosil (highly disperse $SiO_2$) | 0.2 mg | 3.0 g | 0.1% |
| | 146.4 mg | 3000.0 g | 100% |

50 g of the polyethylene oxide, 3 g α-tocopherol and 3 g Aerosil were mixed to a homogeneous mixture by means of a mortar. All the further components were added and mixed for 15 minutes in a free-fall mixer.

Extrusion was performed using a model Micro 27 PH 40 D twin screw extruder manufactured by Leistritz (Nürnberg). Screws having eccentric ends were used. The die used is a heatable round die having a diameter of 9 mm.

The following parameters were selected for extrusion:

| | |
|---|---|
| Screw speed: | 100 rpm |
| Throughput: | 4 kg/h |
| Product temperature: | 134° C. |
| Casing temperature: | heating zones 1 to 10: 100° C. |
| | heating zone 11 (die): 120° C. |

The extrudate, which was still hot, was cooled. No nitrogen atmosphere was used. The product did not exhibit any yellowish discoloration.

The cooled strand was singulated into biplanar slices. The final press-forming was performed by means on an eccentric tablet press (model EK0). Oblong punches (width 5 mm, length 12 mm) were used as tabletting tool. The respective tablets (mass and form) were punched from the slices and press-formed. One tablet was obtained from one slice.

The breaking strength of the tablets was determined with the stated apparatus in accordance with the stated method. The tablets did not crush when exposed to a force of 500 N. The tablet could not be comminuted with a hammer. This could not be achieved with the assistance of a pestle and mortar either.

In vitro release of the active ingredient from the preparation was determined in a paddle stirrer apparatus with sinker in accordance with Pharm. Eur. The temperature of the release medium was 37° C. and the rotational speed of the stirrer 75 min$^-$. 600 ml of artificial intestinal juice, pH 6.8 were used as release medium. The released quantity of active ingredient present in the dissolution medium at each point in time was determined by spectrophotometry.

| Time | Amount Released |
|---|---|
| 60 min | 36% |
| 240 min | 79% |
| 480 min | 99% |
| 720 min | 107% |

EXAMPLE 3

| Components | Per Tablet | Per batch | % |
|---|---|---|---|
| Oxycodon HCl | 20.0 mg | 333.3 g | 11.1 |
| Polyethylene oxide 7 000 000 (Polyox WSR 303, DOW Chemicals) | 122.6 mg | 2060.7 g | 68.7 |
| Polyethylene glycol (PEG 6000) | 18.0 mg | 300.0 g | 10.0 |
| Hypromellose (Metholose 90 SH 100 000 cP, ShinEtsu) | 18.0 mg | 300.0 g | 10.0 |
| α-Tocopherol | 0.2 mg | 3.0 g | 0.1 |
| Aerosil (highly disperse $SiO_2$) | 0.2 mg | 3.0 g | 0.1 |
| | 180 mg | 3000.0 g | 100% |

50 g of the polyethylene oxide, 3 g α-tocopherol and 3 g Aerosil were mixed to a homogeneous mixture by means of a mortar. All the further components were added and mixed for 15 minutes in a free-fall mixer.

Extrusion was performed using a model Micro 27 PH 40 D twin screw extruder manufactured by Leistritz (Nürnberg). Screws having eccentric ends were used. The die used is a heatable round die having a diameter of 9 mm.

The following parameters were selected for extrusion:

| | |
|---|---|
| Screw speed: | 100 rpm |
| Throughput: | 4 kg/h |
| Product temperature: | 134° C. |
| Casing temperature: | heating zones 1 to 10: 100° C. |
| | heating zone 11 (die): 120° C. |

The extrudate, which was still hot, was cooled. No nitrogen atmosphere was used. The product did not exhibit any yellowish discoloration.

The cooled strand was singulated into biplanar slices. The final press-forming was performed by means on an eccentric tablet press (model EK0). Oblong punches (width 5 mm, length 12 mm) were used as tabletting tool. The respective tablets (mass and form) were punched from the slices and press-formed. One tablet was obtained from one slice.

The breaking strength of the tablets was determined with the stated apparatus in accordance with the stated method. The tablets did not crush when exposed to a force of 500 N. The tablet could not be comminuted with a hammer. This could not be achieved with the assistance of a pestle and mortar either.

In vitro release of the active ingredient from the preparation was determined in a paddle stirrer apparatus with sinker in accordance with Pharm. Eur. The temperature of the release medium was 37° C. and the rotational speed of the stirrer 75 min$^{-1}$. 600 ml of artificial intestinal juice, pH 6.8 were used as release medium. The released quantity of active ingredient present in the dissolution medium at each point in time was determined by spectrophotometry.

| Time | Amount released |
|---|---|
| 60 min | 33% |
| 240 min | 76% |
| 480 min | 100% |
| 720 min | 108% |

EXAMPLE 4

| Components | Per tablet | Per batch | % |
|---|---|---|---|
| Tramadol | 116.5 mg | 349.0 g | 34.9 |
| Polyethylene oxide 7 000 000 (Polyox WSR 303, DOW Chemicals) | 150.2 mg | 450.0 g | 45.0 |
| Polyethylene glycol (PEG 6000) | 33.4 mg | 100.0 g | 10.0 |
| Hypromellose (Metholose 90 SH 100 000 cP, ShinEtsu) | 33.4 mg | 100.0 g | 10.0 |
| Butylhydroxytoluene | 0.3 mg | 1.0 g | 0.1 |
| | 333.8 mg | 1000 g | 100% |

45 g of the polyethylene oxide and 1 g butylhydroxytoluene were mixed to a homogeneous mixture by means of a mortar. All the further components were added and mixed for 15 minutes in a free-fall mixer.

Extrusion was performed using a model Micro 27 PH 40 D twin screw extruder manufactured by Leistritz (Nürnberg). Screws having eccentric ends were used. The die used is a heatable round die having a diameter of 9 mm.

The following parameters were selected for extrusion:

| | |
|---|---|
| Screw speed: | 100 rpm |
| Throughput: | 4 kg/h |
| Product temperature: | 134° C. |
| Casing temperature: | heating zones 1 to 10: 100° C. |
| | heating zone 11 (die): 120° C. |

The extrudate, which was still hot, was cooled. No nitrogen atmosphere was used. The product did not exhibit any yellowish discoloration.

The cooled strand was singulated into biplanar slices. The final press-forming was performed by means on an eccentric tablet press (model EK0). Round punches (diameter 10 mm) having a radius of curvature of 8 mm were used as tabletting tool. One tablet was obtained from one slice.

The breaking strength of the tablets was determined with the stated apparatus in accordance with the stated method. The tablets did not crush when exposed to a force of 500 N. The tablet could not be comminuted with a hammer. This could not be achieved with the assistance of a pestle and mortar either.

EXAMPLE 5

| Components | PerTablet | Per batch | % |
|---|---|---|---|
| Oxycodon HCl | 40.00 mg | 133.3 g | 13.3 |
| Polyethylene oxide 5 000 000 (Polyox WSR Coagulant, DOW Chemicals) | 190.0 mg | 643.3 g | 63.3 |

-continued

| Components | PerTablet | Per batch | % |
|---|---|---|---|
| Polyethylene glycol (PEG 6000) | 30.0 mg | 100.0 g | 10.0 |
| Hypromellose (Metholose 90 SH 100 000 cP, ShinEtsu) | 30.0 mg | 100.0 g | 10.0 |
| α-Tocopherol | 5.0 mg | 16.7 g | 1.7 |
| Aerosil (highly disperse SiO$_2$) | 5.0 mg | 16.7 g | 1.7 |
| | 300 mg | 1000 g | 100 |

50 g of the polyethylene oxide, 5 g α-tocopherol and 5 g Aerosil were mixed to a homogeneous mixture by means of a mortar. All the further components were added and mixed for 15 minutes in a free-fall mixer.

Extrusion was performed using a model Micro 27 PH 40 D twin screw extruder manufactured by Leistritz (Nürnberg). Screws having eccentric ends were used. The die used is a heatable round die having a diameter of 9 mm.

The following parameters were selected for extrusion:

| | |
|---|---|
| Screw speed: | 100 rpm |
| Throughput: | 4 kg/h |
| Product temperature: | 134° C. |
| Casing temperature: | heating zones 1 to 10: 100° C. |
| | heating zone 11 (die): 120° C. |

The extrudate, which was still hot, was cooled. No nitrogen atmosphere was used. The product exhibited a slight yellowish coloration. However, this coloration was merely caused by the natural color of α-tocopherol, but was not intensified by the extrusion, i.e. the extrusion was performed without discoloration.

The cooled strand was singulated into biplanar slices. The final press-forming was performed by means on an eccentric tablet press (model EK0). Round punches (diameter 10 mm) having a radius of curvature of 8 mm were used as tabletting tool. One tablet was obtained from one slice.

The breaking strength of the tablets was determined with the stated apparatus in accordance with the stated method. The tablets did not crush when exposed to a force of 500 N. The tablet could not be comminuted with a hammer. This could not be achieved with the assistance of a pestle and mortar either.

In vitro release of the active ingredient from the preparation was determined in a paddle stirrer apparatus with sinker in accordance with Pharm. Eur. The temperature of the release medium was 37° C. and the rotational speed of the stirrer 75 min$^{-1}$. 600 ml of artificial intestinal juice, pH 6.8 were used as release medium. The released quantity of active ingredient present in the dissolution medium at each point in time was determined by spectrophotometry.

| Time | Amount released |
|---|---|
| 60 min | 33% |
| 240 min | 76% |
| 480 min | 100% |
| 720 min | 108% |

The invention claimed is:

1. An abuse-proofed dosage form thermoformed by extrusion without discoloration comprising one or more active ingredients with abuse potential (A), optionally physiologically acceptable auxiliary substances (B), at least one synthetic or natural polymer (C) and optionally at least one wax (D), wherein the dosage form exhibits a breaking strength of at least 500 N, the one or more active ingredients with abuse potential (A) are selected from the group consisting of oxymorphone and physiologically acceptable compounds and derivatives thereof, and the polymer (C) comprises polyethylene oxide having a molecular weight of at least 0.5 million g/mol.

2. The dosage form according to claim 1, which is in the form of a tablet.

3. The dosage form according to claim 1, wherein the molecular weight of the polyethylene oxide (C) is at least 1 million g/mol.

4. The dosage form according to claim 3, wherein the molecular weight of the polyethylene oxide is in the range of from about 1 to about 15 million g/mol.

5. The dosage form according to claim 1, which comprises the wax (D), and the wax (D) is at least one natural, semi-synthetic or synthetic wax with a softening point of at least 60° C.

6. The dosage form according to claim 5, wherein the wax (D) is carnauba wax or beeswax.

7. The dosage form according to claim 1, which additionally comprises:
   (a) at least one substance which irritates the nasal passages and/or pharynx; and/or
   (b) at least one viscosity-increasing agent, which in the presence of an active ingredient extracted from the dosage form using a liquid medium, forms a gel with the extract obtained from the dosage form, which gel optionally remains visually distinguishable when introduced into a further quantity of an aqueous liquid; and/or
   (c) at least one antagonist for the active ingredient or active ingredients with abuse potential; and/or
   (d) at least one emetic; and/or
   (e) at least one dye; and/or
   (f) at least one bitter substance.

8. The dosage form according to claim 7, wherein component (b) is at least one viscosity-increasing agent selected from the group consisting of microcrystalline cellulose combined with carboxymethylcellulose sodium, polyacrylic acid, locust bean flour, pectins, waxy maize starch, sodium alginate, guar flour, iota carrageenan, karaya gum, gellan gum, galactomannan, tara bean flour, propylene glycol alginate, apple pectin, sodium hyaluronate, tragacanth, tara gum, fermented polysaccharide welan gum, and xanthan gum.

9. The dosage form according to claim 1, which comprises at least one active ingredient with abuse potential (A) at least partially in controlled release form.

10. The dosage form according to claim 9, wherein each of the active ingredients with abuse potential (A) is present in a controlled release matrix.

11. The dosage form according to claim 10, wherein the controlled release matrix material comprises component (C) and/or the optionally present component (D).

12. The dosage form according to claim 1, which comprises a core and a tubular domain surrounding the core, wherein said tubular domain has a morphology different from that of the core.

13. The dosage form according to claim 12, wherein the core and the tubular domain have substantially the same chemical composition.

14. The dosage form according to claim 12, wherein the tubular domain does not completely cover the core.

15. The dosage form according to claim 1, which comprises a physiologically acceptable auxiliary substance (B), and the physiologically acceptable auxiliary substance (B) is an antioxidant.

16. The dosage form according to claim 15, wherein the antioxidant is selected from the group consisting of ascorbic acid, salts of ascorbic acid, butylhydroxyanisole, butylhydroxytoluene, monothioglycerol, phosphorous acid, vitamin C, vitamin E and the derivatives thereof, sodium bisulfite and α-tocopherol.

17. A process for the production of a dosage form according to claim 1, comprising:
 I) mixing components (A), the optionally present component (B), (C) and the optionally present component (D);
 II) heating the resultant mixture in the extruder at least up to the softening point of component (C) and extruding the mixture as extrudate through the outlet orifice of the extruder by application of force; and
 III) singulating and forming the still plastic extrudate into the dosage form; or
 IV) cooling and forming the optionally reheated singulated extrudate into the dosage form.

18. The process according to claim 17, wherein process step II) is performed by means of a twin-screw-extruder.

19. The process according to claim 17, wherein process steps II) and III) and optionally process steps I) and IV) are performed under an inert gas atmosphere.

20. The process according to claim 19, wherein nitrogen is used as the inert gas atmosphere.

21. The process according to claim 17, wherein mixing of the components according to process step I) proceeds in the extruder under an inert gas atmosphere.

22. The process according to claim 17, wherein the mixture according to process step I) is extruded through a die with at least one bore.

23. The process according to claim 17, wherein the extrudate is singulated by cutting.

24. The process according to claim 17, wherein the extrudate is in the form of a strand and is shaped and singulated with the assistance of counter rotating calender rolls comprising opposing recesses in their outer sleeve.

25. The process according to claim 17, wherein the singulated extrudate is pelletized or pressed into tablets.

26. The process according to claim 17, wherein swelling and expansion of the dosage form upon storage is suppressed by press forming the singulated extrudate at a pressure of at least 1 kN and a temperature of between 25° C. and 40° C. below the melting range of the mixture of the components.

27. A dosage form according to claim 1, wherein the physiologically acceptable compounds and derivatives are salts, solvates, esters, ethers and amides.

* * * * *